(12) United States Patent
Algar et al.

(10) Patent No.: US 12,631,625 B2
(45) Date of Patent: May 19, 2026

(54) PARTICLE ASSEMBLIES, METHODS OF MAKING AND USE

(71) Applicants: STEMCELL Technologies Canada Inc., Vancouver (CA); The University of British Columbia, Vancouver (CA)

(72) Inventors: Russ Algar, Vancouver (CA); Michael Van Tran, Vancouver (CA)

(73) Assignees: STEMCELL TECHNOLOGIES CANADA INC., Vancouver (CA); THE UNIVERSITY OF BRITISH COLUMBIA, Vancouver (CA)

( * ) Notice: Subject to any disclaimer, the term of this patent is extended or adjusted under 35 U.S.C. 154(b) by 1244 days.

(21) Appl. No.: 16/448,843

(22) Filed: Jun. 21, 2019

(65) Prior Publication Data

US 2020/0400656 A1 Dec. 24, 2020

(51) Int. Cl.
| | |
|---|---|
| *G01N 33/58* | (2006.01) |
| *G01N 1/40* | (2006.01) |
| *G01N 33/543* | (2006.01) |
| *G02B 21/06* | (2006.01) |
| *G02B 21/16* | (2006.01) |
| *G02B 21/36* | (2006.01) |

(52) U.S. Cl.
CPC ....... *G01N 33/5434* (2013.01); *G01N 1/4077* (2013.01); *G02B 21/06* (2013.01); *G02B 21/361* (2013.01)

(58) Field of Classification Search
CPC ............. G01N 33/5434; G01N 1/4077; G01N 33/588; G02B 21/06; G02B 21/361; G02B 21/0008; G02B 21/086; G02B 21/16
See application file for complete search history.

(56) References Cited

U.S. PATENT DOCUMENTS

| | | | | |
|---|---|---|---|---|
| 9,295,736 B2 * | 3/2016 | Margel | .............. | A61K 41/0052 |
| 2010/0112716 A1 * | 5/2010 | Rosenzweig | .......... | B82Y 15/00 |
| | | | | 977/773 |
| 2013/0230858 A1 * | 9/2013 | Cantor | ................ | C12Q 1/6883 |
| | | | | 536/25.4 |

FOREIGN PATENT DOCUMENTS

| | | |
|---|---|---|
| WO | 2007136413 A2 | 11/2007 |
| WO | 2014029012 A1 | 2/2014 |
| WO | 2016061563 A1 | 4/2016 |

OTHER PUBLICATIONS

Chen et al. "Magneto-Fluorescent Core-Shell Supernanoparticles", Nature Communications, 5, Article No. 5093, published 2014 (Year: 2014).*

(Continued)

*Primary Examiner* — Shafiqul Haq
*Assistant Examiner* — Nam P Nguyen
(74) *Attorney, Agent, or Firm* — Smart & Biggar LP; Patricia Folkins

(57) ABSTRACT

The present application is directed to a composite material comprising a core that is responsive to a magnet or a magnetic field, surrounded by a polymer that has been chemically modified to spontaneously bind and assemble a dense corona of fluorescent quantum dots, which is then over-coated with another layer of modified polymer that can be bound by an antibody complex for targeting specific antigens. Methods of preparing and using this material for the detection and quantification of target antigens is also included in the application.

25 Claims, 23 Drawing Sheets

(56) References Cited

OTHER PUBLICATIONS

Earhart et al. "Synthesis of Carbohydrate-Conjugated Nanoparticles and Quantum Dots", Langmuir, 2008, vol. 24, pp. 6215-6219 (Year: 2008).*

Wang et al., "Surface-Functionalizing Metal, Metal Oxide and Semiconductor Nanocrystals with a Multi-coordinating Polymer Platform", MRS Advances, 2016 Materials Research Society, pp. 3741-3747. (Year: 2016).*

Wognum et al., "Use of Tetrameric Antibody Complexes to Stain Cells for Flow Cytometry", Cytometry, 1987, vol. 8, pp. 366-371.

Wilson et al., "Magnetic Microspheres Encoded with Photoluminescent Quantum Dots for Multiplexed Detection", Journal of Materials Chemistry, 2007, vol. 17, pp. 4400-4406.

Mistlberger et al., "Luminescent magnetic particles: Structures, syntheses, multimodal imaging, and analytical applications", Bioanalytical Reviews, 2010, vol. 2(1-4), pp. 61-101, Abstract.

Algar et al., "Semiconductor Quantum Dots in Bioanalysis: Crossing the Valley of Death", Anal. Chem., 2011, vol. 83, pp. 8826-8837.

Zhu H. et al., "Cost-effective and compact wide-field fluorescent imaging on a cell-phone", Lab Chip, 2011, vol. 11(2), pp. 315-322.

Kang et al., "On-site cell concentration and viability detections using smartphone based field-portable cell counter", Anal. Chim. Acta., 2019, vol. 1077, pp. 216-224, Abstract.

Petryayeva et al., "A job for quantum dots: use of a smartphone and 3D-printed accessory for all-in-one excitation and maging of photoluminescence", Anal. Bioanal. Chem, 2016, 408(11), pp. 2913-2925, Abstract.

Petryayeva, E. et al., "Toward point-of-care diagnostics with consumer electronic devices: The expanding role of nanoparticles"; RSC Adv. 2015, 5 (28), pp. 22256-22282, Abstract.

Vashist, S. K. et al., Cellphone-based devices for bioanalytical sciences, Anal. Bioanal. Chem. 2014, 406 (14), pp. 3263-3277.

Petryayeva, E. et al., "Single-step bioassays in serum and whole blood with a smartphone, quantum dots and paper-in-PDMS chips", Analyst 2015, 140 (12), 4037-4045, Abstract.

Ghinwa H. Darwish et al., "Fully Self-Assembled Silica Nanoparticle-Semiconductor Quantum Dot Supra-Nanoparticles and Immunoconjugates for Enhanced Cellular Imaging by Microscopy and Smartphone Camera", ACS Appl. Mater. Interfaces, 2020, vol. 12, pp. 33530-33540.

Zhujun X. et al., "Prototype Smartphone-Based Device for Flow Cytometry with Immunolabeling via Supra-nanoparticle Assemblies of Quantum Dots", ACS Meas. Sci. Au, 2022, vol. 2, pp. 57-66.

* cited by examiner

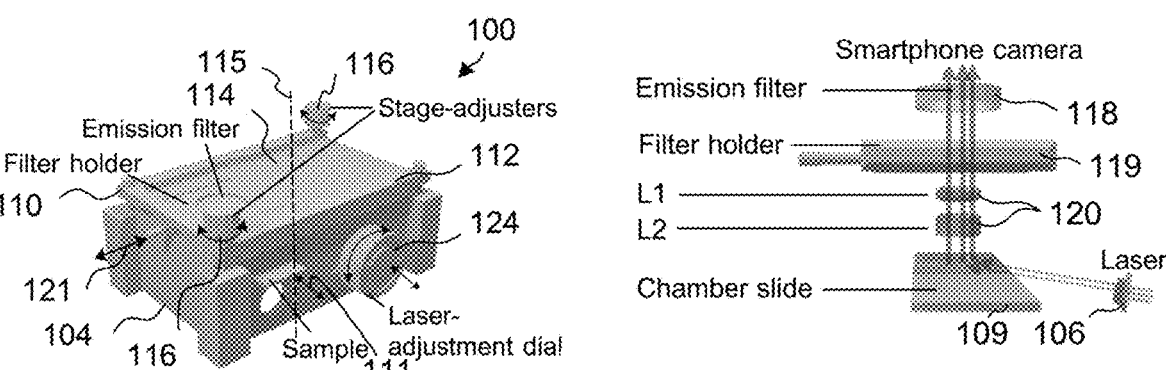
Fig. 2A                    Fig. 2B
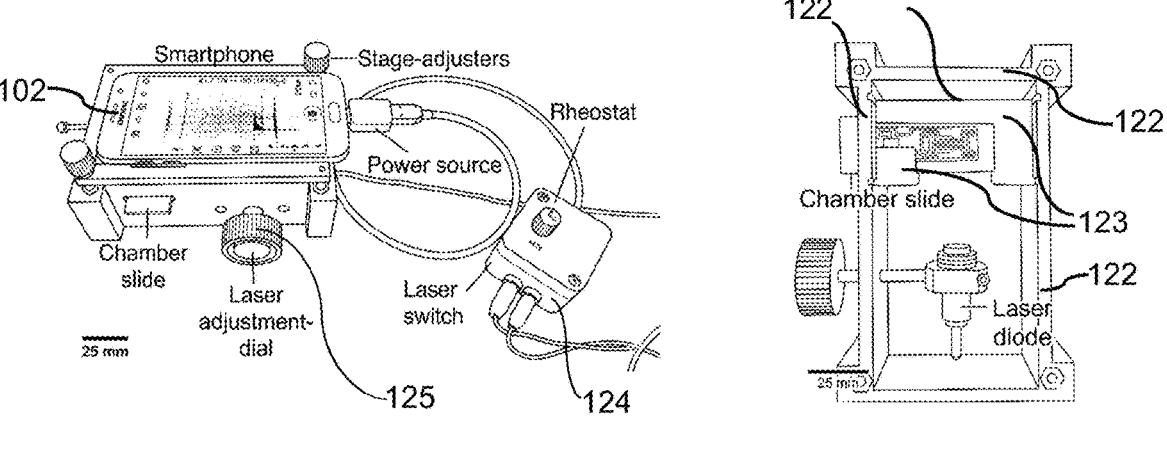
Fig. 2C                    Fig. 2D

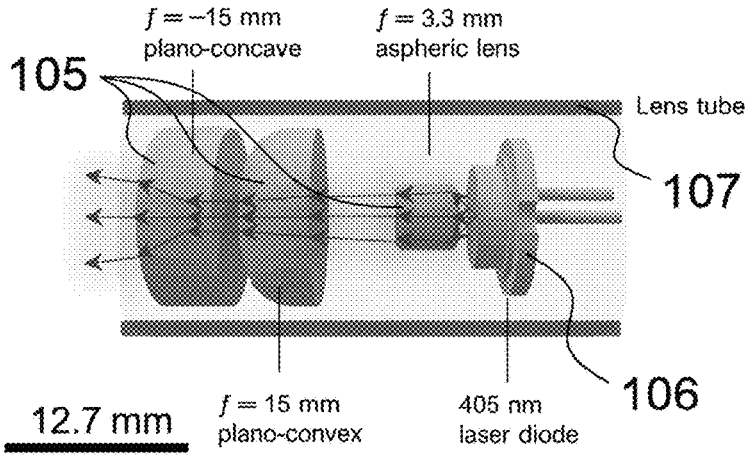
Fig. 6
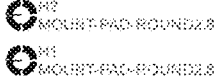
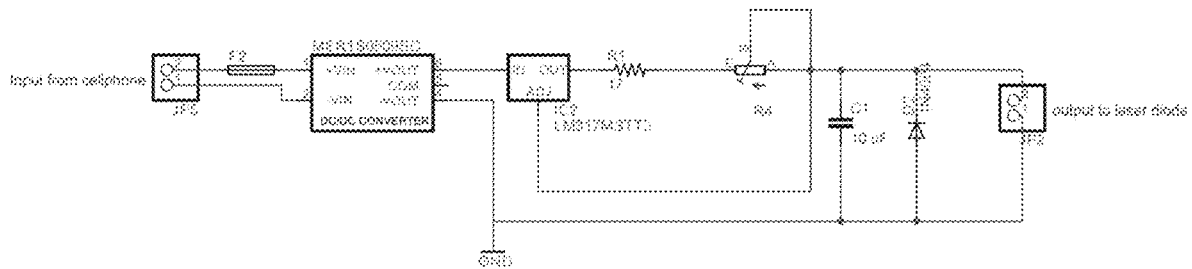
Fig. 7

Fig. 8
Without background subtraction
With background subtraction
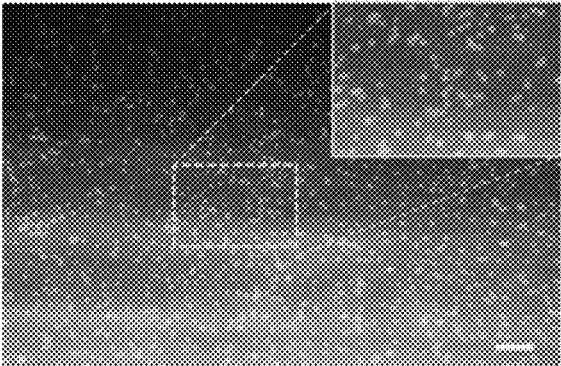 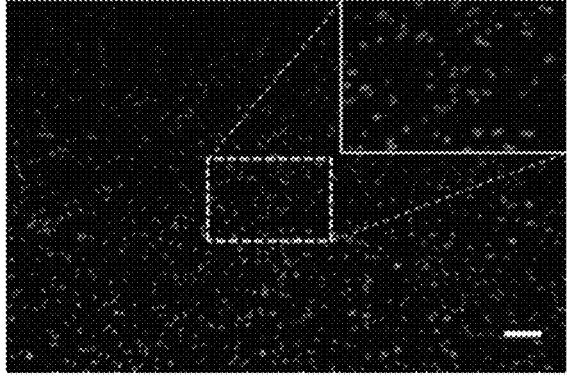
Fig. 9

Before wash step

MNP@QD

MNP@QD + Dex After 15 min. at 60 °C

MNP@QD + API-Dex After 15min. at 60 °C

After 5 min. on benchtop

MNP@QD

After wash step.

MNP@QD + Dex

MNP@QD + API-Dex

PARTICLE ASSEMBLIES, METHODS OF MAKING AND USE

FIELD

The present application is in the field of detection of target antigens, in particular detection of antigens on target entities, including cells, using particle/quantum dot/antibody complex assemblies.

BACKGROUND

Detection and enumeration of specific cell types are useful for diagnostic and therapeutic purposes. For example, in the food industry, the detection of microorganisms helps prevent the spread of foodborne illnesses (Mello, L. D.; Kubota, L. T. Food Chem. 2002, 77 (2), 237-256). There are also many examples of medical applications for the enumeration of specific cell types: CD4$^+$ cell counts are routinely used to diagnose AIDS and monitor the health of patients infected with HIV (Wynberg, E. et al. J. Int. AIDS Soc. 2014, 17 (1), 18809; Barnett, D. et al. Nat. Rev. Microbiol. 2008, 6 (SUPPL. 11), S7-15); hematopoietic progenitor cell counts aid in feasibility assessments for autologous transplantation following ablative chemotherapy and radiation therapy (Gratama, J. W. et al. Commun. Clin. Cytom. 1998, 34 (3), 128-142; Sutherland, D. R.; Keating, A.; Nayar, R.; Anania, S.; Stewart, A. K. Exp. Hematol. 1994, 22 (10), 1003-1010; Gajkowska, A. et al. Folia Histochem. Cytobiol. 2006, 44 (1), 53-60); and tumor cell counts correlate with the status of a cancer in terms of aggression, metastasis, or recurrence, and can help guide treatment (Chaffer, C. L.; Weinberg, R. A. Science. 2011, 331 (6024), 1559-1564). Once samples are collected, the target cell type is frequently isolated or distinguished from non-target cells through immunolabeling of diagnostic cell-surface antigens. For example, the expression level of human epidermal growth factor receptor 2 (HER2) is useful for characterizing breast cancer aggression and the feasibility for therapy with monoclonal antibodies such as Herceptin (Trastuzumab) (Stebbing, J.; Copson, E.; O'Reilly, S. Cancer Treat. Rev. 2000, 26 (4), 287-290). These and many other examples highlight the importance of developing technologies for the enumeration of specific cell types (Boyle, D. S. et al. Trends Biotechnol. 2012, 30 (1), 45-54; Ferreira, M. M.; Ramani, V. C.; Jeffrey, S. S. Mol. Oncol. 2016, 10 (3), 374-394).

Currently, the gold standard technology for enumeration of specific cell types is flow cytometry, which generally relies on fluorescent immunolabeling of cells (Herzenberg, L. A. et al. A. Clin. Chem. 2002, 48 (10), 1819-1827). Flow cytometers are effective at phenotyping (and sometimes sorting) heterogeneous populations of cells, and can provide information about cell size and shape, but their large size, high cost, sophistication, and need for specialized training make them unsuitable for point-of-need applications. Hemocytometers and Coulter counters are other standard cell counting methods (Sun, T.; Morgan, H. Microfluid. Nanofluidics 2010, 8 (4), 423-443; Rayment, E. A.; Williams, D. J. Stem Cells 2010, 28, 996-1004). Although much simpler and far less expensive than flow cytometry, these methods lack the biochemical selectivity and information that comes from fluorescent immunolabeling. Simple, portable, and low-cost technologies that support fluorescent immunolabeling are needed to maximize the prospective benefits of cell counting assays for pathogen detection, health care, and other bioanalyses. To this end, smartphones are an emerging platform for a wide variety of bioanalyses (Petryayeva, E.; Algar, W. R. RSC Adv. 2015, 5 (28), 22256-22282; Vashist, S. K. et al. Anal. Bioanal. Chem. 2014, 406 (14), 3263-3277; Erickson, D. et al. Lab Chip 2014, 14 (17), 3159-3164). Their portability, cost, ubiquity, connectivity, and processing capabilities are amenable to point-of-need and low-resource settings (Petryayeva, E.; Algar, W. R. RSC Adv. 2015, 5 (28), 22256-22282). In the case of optical bioanalyses, the smartphone camera has supported colorimetric (Wang, Y. et al. Anal. Chem. 2017, acs.analchem.7b02139; Berg, B. et al. ACS Nano 2015, 9 (8), 7857-7866; Shen, L.; Hagen, J. A.; Papautsky, I. Lab Chip 2012, 12 (21), 4240), fluorescent (Wei, Q. et al. ACS Nano 2013, 7 (10), 9147-9155; Petryayeva, E.; Algar, W. R. Analyst 2015, 140 (12), 4037-4045; Kong, J. E. et al. ACS Nano 2017, 11 (3), 2934-2943; Jiang, L. et al. Sci. Rep. 2015, 4 (1), 4137; Yu, H.; Tan, Y.; Cunningham, B. T. Anal. Chem. 2014, 86 (17), 8805-8813), phosphorescent (Paterson, A. S. et al. Lab Chip 2017, 17 (6), 1051-1059), and holographic detection (Min, J. et al. ACS Nano 2018, 12 (9), 9081-9090; Tseng, D. et al. Lab Chip 2010, 10 (14), 1787), and the range of analytes has included 2,4-dichlorophenoxy acetic acid (an herbicide) (Wang, Y. et al. Anal. Chem. 2017, 89 (17), 9336-9346), human cytomegalovirus (Wei, Q. et al. ACS Nano 2013, 7 (10), 9147-9155), human alpha-thrombin (Petryayeva, E.; Algar, W. R. Analyst 2015, 140 (12), 4037-4045), and human chorionic gonadotropin (Paterson, A. S. et al. Lab Chip 2017, 17 (6), 1051-1059), among many others.

SUMMARY

The present application relates to compositions, methods, kits and systems involving particle assemblies that are amenable to pairing with a smartphone-based imaging platform (SIP) to enable simple, rapid, and selective cell isolation, fluorescent labeling, and/or counting. One exemplary embodiment of the materials and assay format is outlined in FIG. 1. In this embodiment, the assemblies (denoted MNP@QD) comprise a polymer-coated colloid core surrounded by a dense corona of semiconductor quantum dots (QDs) and are further stabilized with an outer layer of polymer. These assemblies are largely self-assembled through affinity interactions: the polymer on the core is modified with functional groups to bind QDs through coordinate interactions, and immunoconjugates of the MNP@QDs are prepared via tetrameric antibody complexes (TACs). In an exemplary embodiment, one end of the TAC is an anti-polymer antibody that binds to the MNP@QD and the other end of the TAC binds to an antigen on a target cell type. An assay for counting breast cancer cells (e.g. SK-BR3) on the basis of their expression of HER2, including selectivity against a HER2-negative breast cancer cell line (e.g. MDA-MB-231), was developed to show proof of concept. MNP@QD and TAC are spiked into a sample cell suspension, and, after a brief incubation period, a magnet is applied to pellet the SK-BR3 cells via bound MNP@QD-TAC conjugates. The pellet is then washed, resuspended, and transferred into a chamber slide for imaging on the SIP. The cells brightly glow the color of the QD photoluminescence (PL) and cell counts are obtained from the smartphone image. The SIP and MNP@QD materials are both useful toward point-of-need technologies for cell-based assays.

Accordingly, the present application includes a particle assembly comprising:

a. a core that is responsive to a magnetic field;

b. a first polymer coating surrounding the core the first polymer being chemically modified to bind quantum dots;

c. a second polymer over-coating external to the first polymer coating, the second polymer being chemically modified to bind the quantum dots; and d. quantum dots bound to the first polymer coating and the second polymer coating.

The present application also includes a method of preparing a particle assembly of the application comprising:

a. combining a core coated with a first polymer coating and quantum dots under conditions for the self-assembly of the quantum dots with the core coated with the first polymer coating to provide a particle-quantum dot assembly; and b. separating unbound quantum dots from the particle-quantum dot assembly; and c. coating the separated particle-quantum dot assembly from b. with a second polymer.

The present application also includes a method for labelling and/or isolating a target antigen from a mixture comprising:

a. combining the mixture with a particle assembly of the application and a bispecific antibody complex (BAC) comprising an antibody that binds to the second polymer coating, and optionally the first polymer coating, and an antibody that binds to the target antigen to form a particle assembly-BAC-target antigen conjugate;

b. applying a magnet or a magnetic field to the mixture to separate the particle assembly-BAC-target antigen conjugate from the mixture; and c. optionally isolating the particle assembly-BA-target antigen conjugate.

The present application also includes a method for detecting and, optionally quantifying a target antigen in a mixture comprising:

a. combining the mixture with a particle assembly of the application and a bispecific antibody complex (BAC) comprising an antibody that binds to the second polymer coating, and optionally the first polymer coating, and an antibody that binds to the target antigen to form a particle assembly-BAC-target antigen conjugate;

b. applying a magnet or a magnetic field to the mixture to separate the particle assembly-BAC-target antigen conjugate from the mixture;

c. isolating the particle assembly-BAC-target antigen conjugate; and d. imaging the particle assembly-BAC-target antigen conjugate, wherein a positive image indicates a presence of the target antigen in the mixture, and optionally, the intensity of the positive image is used to quantify the target antigen in the mixture.

In some embodiments, imaging is performed using an imaging platform, the imaging platform including: an imaging device having a camera; an imaging housing having a sample mount shaped to hold a sample of the magnetic particle assembly-BAC-target antigen conjugate in a sample position, and an imaging platform mount shaped to hold the imaging device in an imaging device position, the imaging device position directing the camera towards the sample position; a laser source positioned to illuminate the sample position; and a power source coupled to the laser source to provide a power supply to the laser source.

In some embodiments, the imaging platform further includes at least one beam-shaping lens between the laser source and the sample position, at least one magnifying lens between the sample position and the imaging device position, and an emission filter between the at least one magnifying lens and the imaging device position.

In some embodiments, the imaging device mount is a stage shaped to support a body of the imaging device, the stage positioned above the sample mount and selectively vertically translatable relative the sample mount.

In some embodiments, the imaging platform further includes at least one thumb-screw stage-adjuster governing the vertical translation of the stage relative the sample mount.

In some embodiments, the imaging housing encloses the sample position and the laser source within a housing interior formed by a set of sidewalls overlaid by the stage, the stage including an imaging aperture through which the imaging device position directs the camera.

In some embodiments, the emission filter is removably received in the imaging aperture and selectively vertically translatable along with the stage, the emission filter slidably removable from the imaging aperture along a filter removal path which does not pass through the imaging device position.

In some embodiments, the imaging device is a smartphone.

In some embodiments, the power source is a battery of the smartphone.

In some embodiments, the intensity of the laser source is adjustable by modifying the power supply.

In some embodiments, the imaging platform further includes a rheostat coupled between the laser source and the power source, and the power supply may be modified using the rheostat.

In some embodiments, the imaging platform further includes at least one laser dial coupled to the laser source to adjust an angle of the laser and a distance between the laser source and the sample position.

In some embodiments, the sample mount is shaped to removably receive a chamber slide in which the sample is contained, the chamber slide slidably removable from the housing along a chamber removal path which does not pass through the imaging device position.

Other features and advantages of the present application will become apparent from the following detailed description. It should be understood, however, that the detailed description and the specific examples while indicating embodiments of the application are given by way of illustration only, the scope of the claims should not be limited by the embodiments set forth in the examples, but should be given the broadest interpretation consistent with the description as a whole.

BRIEF DESCRIPTION OF THE DRAWINGS

The embodiments of the application will now be described in greater detail with reference to the attached drawings in which:

FIG. 2A shows a rendering of an exemplary smartphone-based fluorescent cell imaging platform (SIP). FIG. 2B shows an exemplary optical design for imaging (L1, f=25 mm plano-convex; L2, f=19 mm achromatic doublet lens; emission filter). The laser is 20 mW at a wavelength of ~405 nm. The laser beam-shaping optics are omitted for clarity but can be found in FIG. 6. FIG. 2C is a photo of the exemplary SIP with the smartphone mounted. The thumb-screw stage-adjusters are used for manual focusing. The laser-adjustment dial modifies the angle and lateral position of the laser. The smartphone powers the laser diode, the output intensity of which can be adjusted with the rheostat. FIG. 2D is a photo of the exemplary SIP with top stage removed for a top-down view, with the sample slide illuminated by the laser.

FIG. 6 shows a representation of exemplary laser diode optics. The dispersed light from the laser diode is focused through an aspheric lens (f=3.3 mm) and a plano-convex lens (f=15 mm), then diverged by a plano-concave lens (f=-15 mm).

FIG. 7 shows a circuit diagram for the exemplary rheostat that controlled the exemplary laser diode output intensity.

FIG. 8 shows synthetic scheme for exemplary API-modified dextran. The R group in the final product may be another secondary-amine linkage to API or remaining unreacted (e.g. aldehyde or hemi-acetal).

FIG. 9 shows SIP-acquired images of exemplary MNP@QD605-labeled cells before (left) and after (right) background subtraction in ImageJ. Scale bar=200 μm (except digitally-zoomed inset).

FIG. 15A shows pellet of exemplary MNP@QDs shortly after initial preparation. FIG. 15B shows flocculation of exemplary MNP@QDs when incubated with unmodified dextran. FIG. 15C shows colloidally stable exemplary MNP@QD over-coated with exemplary API-Dex after the same incubation period. FIG. 15D shows as-prepared exemplary MNP@QD after pelleting the particles, followed by removing the supernatant, and then washing the pellet with fresh carbonate buffer. FIG. 15E and FIG. 15F show the exemplary particles were resuspended in fresh buffer and then allowed to incubate on the benchtop for 5 min. exemplary MNP@QD incubated with either unmodified dextran (FIG. 15E) or API-Dex (FIG. 15F). All photographs were taken under ambient lighting conditions. The arrows indicate sample pelleting or flocculation.

DESCRIPTION OF VARIOUS EMBODIMENTS

I. Definitions

Figure 1A:
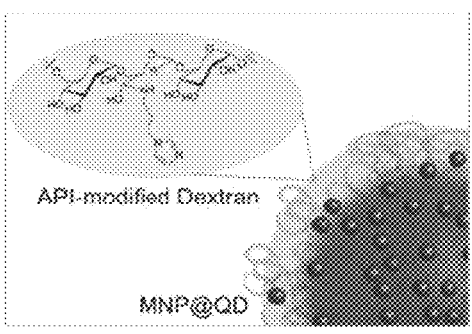
FIG. 1A is a schematic of an exemplary MNP@QD nanoparticle assembly. QDs are bound to an imidazole-modified dextran coating on the IONPs and over-coated with additional imidazole-modified dextran.
Figure 1B:
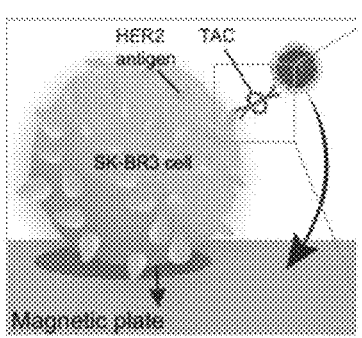
FIG. 1B is a schematic of tetrameric antibody complexes (TAC)-mediated binding of an exemplary MNP@QD to HER2 antigen on the surface of an SK-BR3 cell and isolation by magnetic pull-down.

Unless otherwise indicated, the definitions and embodiments described in this and other sections are intended to be applicable to all embodiments and aspects of the present application herein described for which they are suitable as would be understood by a person skilled in the art.

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a quantum dot" should be understood to present certain aspects with one quantum dot or two or more additional quantum dots.

In embodiments comprising an "additional" or "second" component, the second component as used herein is different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation or analysis to be performed, and the identity of the molecule(s) to be transformed or analysed, but the selection would be well within the skill of a person trained in the art.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "nanoparticle" as used here refers to particles having at least one dimension that is less than about 1000 nm in size.

The term "colloid" as used herein refers to a homogeneous noncrystalline substance consisting of large molecules or ultramicroscopic particles of one substance dispersed through a second substance.

The term "quantum dot" as used herein refers to tiny particles or nanocrystals of a semiconducting material with diameters in the range of 2-20 nanometers and which possess fluorescence properties. The nanocrystals can produce distinctive colors when excited, for example using lasers, generally determined by the size and composition of the particles.

II. Particles of the Application

A composite material with susceptibility to a proximate magnetic field and exceptionally bright and tunable fluorescence has been prepared and described herein. The proximity of the magnetic field to the composite material is a function of at least the quantity of susceptible elements therein. The composite material is a particle assembly composed of a core that is susceptible to a magnetic field, surrounded by a first polymer that has been chemically modified to spontaneously bind and assemble a dense corona of fluorescent quantum dots, and then over-coated with another layer of modified polymer. The first polymer layer or the over-coating may be bound by an at least bispecific antibody complex, such as a tetrameric antibody complex for targeting specific antigens. This composite material can be assembled very simply through spontaneous and strong non-covalent interactions, with simple purification, and plug-and-play utility for different colors of fluorescence and targeting antibodies.

Accordingly, in some embodiments the present application includes a particle assembly comprising:

a. a core that is responsive to a magnetic field;

b. a first polymer coating surrounding the core the first polymer being chemically modified to bind quantum dots;

c. a second polymer over-coating external to the first polymer coating, the second polymer being chemically modified to bind the quantum dots; and d. quantum dots bound to the first polymer coating and the second polymer coating.

In some embodiments, the core comprises metal elements. In some embodiments, the metal elements are in solution format such as ferrofluids, colloids and particles in suspension. In some embodiments, the core is an iron oxide nanoparticle, but can be any composition that is permanently or temporarily magnetizable within a magnetic field. In some embodiments, the core is paramagnetic or superparamagnetic, but can be ferromagnetic. In some embodiments, the core has an average size in at least one direction of about 20 nanometers (nm) to about 2 micrometers ($\mu$m), about 50 nm to 1 $\mu$m, about 75 nm to about 500 $\mu$m, or about 100 nm to about 250 nm.

In some embodiments, the core comprises iron and optionally at least one other metal. In some embodiments, the at least one other metal is gold. In some embodiments, the core is an iron oxide nanoparticle.

The core is coated or contained within a polymer matrix that provides functional chemical groups (e.g. imidazole, etc.) for binding to quantum dots. In some embodiments, the binding between the polymer and the quantum dots is non-covalent. Cores susceptible to a magnetic field and/or magnetic particles pre-coated with a first polymer coating are available from numerous different commercial sources, such as STEMCELL Technologies, Inc. for example, Dextran RapidSpheres™, or can be synthesized using state of the art methods. See Table 1 for a list of exemplary polymer coated core materials.

TABLE 1

| Magnetic Particle Suppliers | | |
| --- | --- | --- |
| Supplier | Product Name | Surface coating |
| Stemcell Technologies | Dextran RapidSpheres ™ | Dextran |
| Ademtech | Adembeads | Polymer |
| Bangs | Promag1 | Polymer |
| Bioclone | BcMag | Silica |
| Chemicell | Fluidmag-ARA | Polysaccharide |
| Chemicell | Simag | Silica |
| Magnedics | MagSi-S | Silica |
| Micromod | Nanomag-CLD | Polysaccharide |
| Micromod | Sicastar-M | Silica |
| Solulink | Nanolink | Polystrene |
| Spherotech | SPHERO Particles | Polystrene |

In some embodiments, the first and second polymer may be the same or similar and may be any polymer that is useful in the particle assemblies and methods described herein. Polymers described in this application can be prepared or synthesized by known techniques or obtained commercially. In some embodiments, the polymers are amphiphilic or hydrophilic and may or may not be homopolymers (containing the same repeating subunits). In some embodiments, the polymers include, but are not limited to, poly(ethylene glycol) (PEG), PEG derivatives, poly(carboxybetaine), dextran, starch, heparin, chitin, cellulose, other polymers of cyclic sugars, synthetic polymers with high anti-fouling properties, peptides or nucleic acids. PEG derivatives include, but are not limited to, non-ionic surfactants such as Tween 20 or 80, Triton X-100 and Pluronic F68 (CAS #9003-11-6, also known as Poloxamer 188, Lutrol F68, Kolliphor P188 or chemically as poly(ethylene glycol)-block-poly(propylene glycol)-block-poly(ethylene glycol)).

In some embodiments, the first and second polymers are the same polymer or are comprised of the same or similar monomers.

The first polymer can be any size but in some embodiments has a molecular weight above 1 kDa, above 5 kDa or above 8 kDa. The second polymer can be any size but in some embodiments, has a molecular weight above 1 kDa, above 5 kDa or above 8 kDa.

In some embodiments, the first and second polymer are dextran. In some embodiments, the dextran polymer has a molecular weight of about 5 KDa to about 20 KDa, or about 6 kDa to about 11 kDa.

In some embodiments, the first and second polymers are chemically modified to include one or more functional groups that bind the quantum dots. In some embodiments, binding between the first and second polymers (as intermediated by the functional groups) and the quantum dots is non-covalent. In some embodiments, the one or more functional groups that non-covalently bind the quantum dots are selected from a thiol group and an imidazole group, suitably an imidazole group. In some embodiments, the first and second polymers are chemically modified to include an imidazole group by reaction with 1-(3-aminopropyl)imidazole (API).

In some embodiments, the first polymer and, optionally the second polymer, is cross-linked prior to being chemically modified to bind the quantum dots, which binding may be covalent or non-covalent.

In some embodiments, the first and second polymer are the same.

In some embodiments, the quantum dots comprise Cd, Pb, Se, Zn and/or S. In some embodiments, the quantum dots are CdSe/CdS/ZnS or CdZNSe/CdZn/ZnS quantum dots. In some embodiments, the quantum dots are ligand stabilized. In some embodiments, the ligand is histidine, glutathione and/or zwitterionic compact ligand 4 (CL4).

In some embodiments, the assembly is a nanoparticle assembly.

In some embodiments, the assembly further comprises an at least bispecific antibody complex, or more specifically a tetrameric antibody complex, comprising an antibody that binds to the second polymer over-coating, and optionally the first polymer coating, and an antibody that binds to a target antigen. In some embodiments, the assembly further comprises an at least bispecific antibody complex, or more specifically a tetrameric antibody complex, comprising an antibody that binds to the second polymer over-coating and an antibody that binds to a target antigen.

In some embodiments, the antibody is an antibody or fragment thereof. Antibody fragments include, but are not limited to, Fab, Fab', F(ab)'$_2$, scFv or single domain fragments. The antibodies or fragments thereof can be prepared using standard techniques known in the art.

In some embodiments, the antibody that binds to the target antigen has high-affinity. As an example, high-affinity antibodies are considered to have equilibrium dissociation constants (K$_d$) smaller than $1\times10^{-7}$M (100 nM).

Polyclonal antibodies against selected antigens may be readily purchased from known purveyors, such as STEM-CELL Technologies, Inc., or generated by one of ordinary skill in the art from a variety of warm-blooded animals such as horses, cows, various fowl, rabbits, mice, or rats.

In some embodiments, monoclonal antibodies are used in the methods and compositions of the application. Monoclonal antibodies specific for selected antigens may be readily purchased from known purveyors, such as STEMCELL Technologies, Inc., or generated using conventional techniques (see, for example, U.S. Pat. No. RE 32,011, U.S. Pat. Nos. 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," Science 246:1275-1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728-5732, August 1989; see also Michelle Alting-Mees et al., "Monoclonal Antibody Expression Libraries: A Rapid Alternative to Hybridomas," Strategies in Molecular Biology 3:1-9, January 1990; these references describe a commercial system available from Stratacyte, La Jolla, Calif., which enables the production of antibodies through recombinant techniques).

Similarly, antibodies may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™. H or ImmunoZAP™. L (Stratacyte), respectively. These vectors may then be introduced into an expression system, including but not limited to an appropriate *E. coli* strain. Utilizing these techniques, large amounts of a single-chain protein containing a fusion of the V$_H$ and V$_L$ domains may be produced (See Bird et al., Science 242:423-426, 1988). In addition, such techniques may be utilized to change a "murine" antibody to a "human" antibody, without altering the binding specificity of the antibody.

Antibodies against selected antigens on the surface of the biological target or directed against the polymer may also be obtained from commercial sources. High-affinity antibody ligands against various polymers are commercially available (see for example, Table 2). For instance, a mouse monoclonal IgG1 antibody recognizing the repeating units of dextran (clone DX1) is available from STEMCELL Technologies. The recent development of anti-PEG antibodies stems from the demand for quantitative methods to assess PEGylation/conjugation of drugs or therapeutics. As a result, monoclonal anti-PEG antibodies that recognize the repeating units of PEG are available from multiple suppliers including Silverlake Research, Life Diagnostics and others (performance data in FIG. 20). The simplicity and wide availability of the polymers and anti-polymer antibodies make them attractive over labeling techniques (for cell separation and fluorescence applications) that rely on expensive and laborious recombinant protein or antibody methods to generate the required binding partners.

TABLE 2

| | Alpha-polymer Antibody Ligand Suppliers | | | | |
|---|---|---|---|---|---|
| Supplier | Polymer Antigen | Clone | Species | Isotype | Affinity |
| STEMCELL Technologies | Dextran | DX1 | Mouse | IgG1 | |
| Silverlake Research | PEG | CH2074 | Mouse | IgG1 | |
| Silverlake Research | PEG | CH2076 | Mouse | IgG1 | |
| Academia Sinica | PEG | E11 | Mouse | IgG1 | |
| Academia Sinica | PEG | 3.3 | Mouse | IgG1 | |
| Maine Biotechnology | PEG | 09F02 | Mouse | IgG3 | |
| Maine Biotechnology | PEG | 26A04 | Rat | IgM | |

TABLE 2-continued

| | | Alpha-polymer Antibody Ligand Suppliers | | | |
|---|---|---|---|---|---|
| Supplier | Polymer Antigen | Clone | Species | Isotype | Affinity |
| Academia Sinica | PEG | APG4 | Mouse | IgM | > than APG3 |
| Life Diagnostics | PEG | 1D9-6 | Mouse | IgG1 | $2.88 \times 10^{\wedge}{-}9M$ |
| Life Diagnostics | PEG | 3F12-1 | Mouse | IgG1 | $1.84 \times 10^{\wedge}{-}9M$ |
| Life Diagnostics | PEG | 10B4-2 | Mouse | IgG1 | $2.28 \times 10^{\wedge}{-}9M$ |
| Life Diagnostics | PEG | 10E3-1-4 | Mouse | IgG1 | $3.7 \times 10^{\wedge}{-}9M$ |
| Life Diagnostics | PEG | 9B5-6-25-7 | Mouse | IgG1 | $1.8 \times 10^{\wedge}{-}9M$ |
| Life Diagnostics | PEG | PEGPAB-1 | Rabbit | IgG | |
| abcam/Epitomics | PEG | PEG-B-47 | Rabbit | IgG | $13.57 \times 10^{\wedge}{-}10M$ |
| abcam | PEG | PEG-2-128 | Rabbit | IgM | |
| abcam | PEG | 26A04 | Rat | IgM | |
| Biovision | PEG | 2M41 | Mouse | IgG2a | |
| Genscript | PEG | 5E10E9 | Mouse | IgM | |
| ANP Tech | PEG | ANPEG-1 | | IgM | |
| USBiological | PEG | 9E454 | Rabbit | IgG | |
| USBiological | PEG | 9L570 | Mouse | IgG1 | |
| Rockland | pHIS | 33D10.D2.G8 | Mouse | IgG1 | |
| Biolegend | pHIS | J099B12 | Mouse | IgG1 | |
| AbD Serotec | Heparin | T320.11 | Mouse | IgG1 | |

In some embodiments, an antibody that binds to a biological target is linked to the antibody that binds the first polymer, and optionally the first polymer coating, using a bispecific antibody complex such as a tetrameric antibody complex (TAC). In a TAC, the two antibodies are linked using a third antibody that binds to the Fc region of the two antibodies. In particular, a TAC may be prepared by mixing a first monoclonal antibody which is capable of binding to the biological target, and a second monoclonal antibody that binds to the first polymer. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the $F(ab')_2$ fragments of monoclonal antibodies of a second animal species which are directed against the Fc-fragments of the antibodies of the first animal species (see for example U.S. Pat. No. 4,868,109 to Lansdorp, which is incorporated herein by reference for a description of tetrameric antibody complexes and methods for preparing same).

In some embodiments, the target antigen is any target that one wishes to separate from a sample, including but not limited to cells, cellular organelle, extracellular vesicles (e.g. exosomes), viruses, prions, DNA, RNA, antibodies, proteins, peptides and small molecules.

In some embodiments, the target antigen is comprised on a cell including cells of any type or lineage such as stem cells, progenitor cells, fetal cells and mature cells. In some embodiments, the cell is a pathogen, an immune cell or a diseased cell. In some embodiments, the diseased cell is a tumor cell.

In some embodiments, the present application also includes an immunoconjugate comprising an assembly of the application. The immunoconjugate comprises the particle assembly, the bispecific antibody complex (BAC, e.g. tetrameric antibody complex (TAC)) and the target antigen (MP@BAC@target antigen).

The brightness of the particle assemblies of the application is enabling in two contexts: (1) in general, it enables simple and rapid target counting on a smartphone-based device, and (2) it specifically enables a minimally engineered (i.e. simple) device to be effective for this purpose.

III. Methods of Producing Particles of the Application

The present application includes a unique self-assembly approach for the preparation of the composite particle materials of the application. In some embodiments the self-assembly at least partly relies on non-covalent interactions. For example, core particles coated with a polymer modified to bind quantum dots, water soluble quantum dots, polymers modified to bind the quantum dots and bispecific antibody components can all be separately prepared, stored and optionally packaged for eventual use. In use, these components can then be mixed and matched off-the-shelf materials with any desired color of fluorescence and targeting antibody. This is possible without covalent chemistry or chemical activation or coupling reagents/crosslinkers, and with minimal and simple purification (e.g. magnetic isolation and washing rather than chromatography columns, spin filtration, dialysis, tangential flow filtration, flow fractionation, electrophoresis, etc.).

Accordingly the present application also includes a method of preparing a particle assembly of the application comprising:

a. combining a core coated with a first polymer coating and quantum dots under conditions for the self-assembly of the quantum dots with the core coated with the first polymer coating to provide a particle-quantum dot assembly; and b. separating unbound quantum dots from the particle-quantum dot assembly; and c. coating the separated particle-quantum dot assembly from b. with a second polymer.

In some embodiments the core coated with the first polymer coating is chemically modified to bind the quantum dots by:

a. activating the first polymer for reaction with a reagent to covalently attach one or more functional groups that bind the quantum dots; and b. reacting the activated first polymer with the reagent.

In some embodiments, the first polymer is dextran and the activating is oxidation to produce aldehyde groups. In some embodiments, the one or more functional groups on the first polymer that binds the quantum dots is a functional group that non-covalently binds the quantum dots. In some embodiments, the one or more functional groups that non-covalently bind the quantum dots is selected from a thiol group and an imidazole group. In some embodiments, the one or more functional groups that non-covalently bind the quantum dots is an imidazole group and the imidazole group is incorporated by reaction of the aldehyde groups with 1-(3-aminopropyl)imidazole (API) under reductive amination conditions.

In some embodiments, the second polymer is dextran that has been modified to bind the quantum dots. In some embodiments, the modified dextran is prepared by:

a. activating the dextran for reaction with a reagent to covalently attach one or more functional groups that bind the quantum dots; and b. reacting the activated first polymer with the reagent.

In some embodiments, the dextran is activated by oxidation to produce aldehyde groups. In some embodiments, the one or more functional groups on the second polymer that bind the quantum dots is a functional group that non-covalently binds the quantum dots. In some embodiments, the one or more functional groups that non-covalently bind the quantum dots is selected from a thiol group and an imidazole group. In some embodiments, the one or more functional groups that non-covalently bind the quantum dots is an imidazole group and the imidazole group is incorporated by reaction of the aldehyde groups of the activated dextran with 1-(3-aminopropyl)imidazole (API) under reductive amination conditions.

In some embodiments, the unbound quantum dots are separated from the particle-quantum dot assembly, and/or the coated separated particle-quantum dot assembly is isolated, by magnetic separation. Magnetic separation means to apply a magnet or a magnetic field in proximity of a solution or mixture comprising the material susceptible to a magnetic field, thereby causing the material to be attracted to the magnet or magnetic field and separate from the portions of the solution not susceptible to a magnet or magnetic field.

In some embodiments, the particle-quantum dot assembly is a nanoparticle-quantum dot assembly.

IV. Methods, Systems and Kits for Detecting a Target

The present application also includes a method for labelling and/or isolating a target antigen from a mixture comprising:

a. combining the mixture with a particle assembly of the application and a bispecific antibody complex (BAC) comprising an antibody that binds to the second polymer coating, and optionally the first polymer coating, and an antibody that binds to the target antigen to form a particle assembly-BAC-target antigen conjugate;

b. applying a magnet or a magnetic field to the mixture to separate the particle assembly-BAC-target antigen conjugate from the mixture; and c. optionally isolating the particle assembly-BAC-target antigen conjugate.

The present application also includes a method for detecting and, optionally quantifying a target antigen in a mixture comprising:

a. combining the mixture with a particle assembly of the application and a bispecific antibody complex (BAC) comprising an antibody that binds to the second polymer coating, and optionally the first polymer coating, and an antibody that binds to the target antigen to form a particle assembly-BAC-target antigen conjugate;

b. applying a magnet or a magnetic field to the mixture to separate the particle assembly-BA-target antigen conjugate from the mixture;

c. isolating the particle assembly-BAC-target antigen conjugate; and d. imaging the particle assembly-BAC-target antigen conjugate, wherein a positive image indicates a presence of the target antigen in the mixture, and optionally, the intensity of the positive image is used to quantify the target antigen in the mixture.

In some embodiments, imaging step d. occurs after the combining step a. and before either the applying step b. or the isolating step c.

In some embodiments the bispecific antibody complex (BAC) comprises an antibody that binds to the second polymer coating and an antibody that binds to the target antigen. In some embodiments, the bispecific antigen complex is a tetrameric antibody complex (TAC). and optionally the first polymer coating, In some embodiments, the target antigen is comprised on a target particle to be detected and/or isolated. In some embodiments, the target particle is a cell. In some embodiments, the cell is a pathogen, an immune cell or a diseased cell. In some embodiments, the diseased cell is a tumor cell.

In some embodiments the mixture is a biological sample, such as a biological sample from a subject. In some embodiments subject is human or an animal. In some embodiments, the subject has a disease, disorder or condition or is suspected of having a disease, disorder or condition and the method is used for diagnosis.

In some embodiments, the imaging of the particle assembly-BAC-target antigen conjugate is done by applying a laser to a suspension of the particle assembly-BAC-target antigen conjugate in a suitable solvent. In some embodiments, the suitable solvent is an aqueous buffer.

From a workflow standpoint, it is generally unusual that excess particles (i.e. unbound to target antigen) do not need to be washed away. In the methods of the application, excess particle assemblies of the application (i.e. MP and MP@BAC) are isolated alongside target antigen labeled with these assemblies, and individual target antigens can be still imaged with high signal-to-background/noise ratios.

The present application further includes kits comprising the particles of the application or various components thereof. For example, in some embodiments, the kits comprise one or more of (i) core particles coated with a polymer modified to bind quantum dots; (ii) water soluble quantum dots; (iii) polymers modified to non-covalently bind the quantum dots and (iv) BA components. In use, these components can then be mixed and matched off-the-shelf materials with any desired color of fluorescence and targeting antibody. In some embodiments, the kits further include instructions for the use thereof in the methods described herein. In some embodiments, the kits are customized depending on the nature of the target antigen. For cell separation methods, the kits can include antibody combinations for depleting unwanted cells and/or enriching for wanted cells. The antibodies that bind to the cells can be linked to the anti-polymer antibody, suitably in a tetrameric antibody complex (TAC) as described above. In some embodiments, the kits further include buffers, microscope slides, cover slips, sample tubes pipettes, magnetic field applicator and/or other reagents known in the art for performing the methods of the application.

The susceptibility to a magnetic field and bright fluorescence properties of the materials described herein allow selective target isolation and imaging that, in some embodiments, can be carried out on an imaging platform.

In some embodiments, the imaging platform includes an imaging device, an imaging housing, a laser source, and a power source. An example of an imaging platform 100 may be seen in FIGS. 2A to 2D. Imaging platform 100 includes an imaging device 102, an imaging housing 104, a laser source 106, and a power source (not shown). In the imaging platform 100 the imaging device 102 is a smartphone, the imaging housing is a 3D printed box, the laser source is a single 405 nm laser diode, and the power supply is a battery of the smartphone 102.

In some embodiments, the imaging device may include a camera for taking an image. In example imaging platform 100, smartphone 102 includes a rear camera (not shown) of smartphone 102 is provided for use as part of imaging platform 100. In some embodiments, a camera is used which is able to image non-visible radiation, such as infrared radiation. For example, a camera may be configured to image electromagnetic radiation having a wavelength between 300 nm and 1100 nm.

The imaging housing may have a sample mount shaped to hold a sample in a sample position. In example imaging platform 100, housing 104 includes a set of sidewalls 122 and projections 123, and a sample mount 108 is formed from sidewalls and projections which are shaped to slidably receive a chamber slide containing a sample. A chamber slide may be slid through an aperture in a sidewall 122 and received by projections 123. Chamber slide 109 may be slide along path 111 which does not pass through the imaging device position, which allows the chamber slide 109 to be removed or inserted without disturbing an imaging device in the imaging device position.

The imaging housing may also have an imaging device mount shaped to hold the imaging device in an imaging device position, the imaging device position directing the camera towards the sample position to enable the camera to image a sample held in the sample position. For example, the stage may be a substantially rectangular plate having a recess on a top side shaped to receive a smartphone, the smartphone held in the recess by gravitational forces. Imaging platform 100 includes an imaging device mount 110. Imaging device mount 110 is a movable stage 112 with a recess 114 to hold the body of smartphone 102. Stage 112 may be selectively translated vertically along vertical axis 115.

The laser source may be positioned to illuminate the sample position to enable the laser source to illuminate the sample when the sample is held in the sample position. The power source may be coupled to the laser to provide a power supply to the laser. For example, imaging platform 100 includes a 405 nm laser diode 106 which is coupled to a battery (not shown) of smartphone 102 by a power cable to receive a power supply from the battery. The power cable couples the laser diode 106 to a port of the smartphone 102 to draw power from an internal batter of smartphone 102. In other embodiments, other power sources could be used. For example, in some embodiments a portable power pack, such as provided to recharge a smartphone, may be used.

In some embodiments, the imaging platform further includes at least one beam-shaping lens between the laser source and the sample position. Beam-shaping lenses may be provided to improve illumination of a sample by the laser source, such as to control beam divergence and convergence along a path between the laser source and the sample position. Imaging platform 100 includes beam shaping lenses 105. Beam shaping lenses 105 are omitted from FIGS. 2A to 2D for clarity, but are shown in FIG. 6. Beam shaping lenses 105 include, in order from laser source 106, an aspheric focusing lens (f=3.3 mm), a plano-convex focusing lens (f=15 mm), and a plano-concave lens (f=−15 mm) to diverge the beam. Beam shaping lenses 105 are contained with laser source 106 in lens tube 107.

In some embodiments, the imaging platform further includes at least one magnifying lens between the sample position and the imaging device position. For example, a magnification lens may be used to direct the camera of the imaging device to a field of view having a chosen size and position. In imaging platform 100 of FIGS. 2A to 2D includes two half-inch magnifying lenses 120 positioned above the sample position occupied in FIG. 2B by chamber slide 109.

In some embodiments, the imaging platform further includes an emission filter between the at least one magnifying lens and the imaging device position. In some embodiments, an emission filter may be used to capture an image of a particular range of wavelengths. For example, where multiple wavelengths of florescence are expected from a sample which has absorbed radiation from the laser source, a user may apply a filter to select which wavelengths are processed. In some embodiments, the imaging device itself includes an emission filter. In some embodiments, an emission filter is applied in software after an image is captured. Imaging device or software filters may be in addition to or in alternative to a filter included as part of the imaging platform.

In some embodiments, the emission filter is removably received in the imaging aperture and selectively vertically translatable along with the stage, the emission filter slidably removable from the imaging aperture along a filter removal path which does not pass through the smartphone position. The configuration of the filter removal path may be provided to allow the emission filter to be removed by a user without repositioning the smartphone, such as to allow a user to interchange filters between image capture events. Imaging platform 100 includes emission filter 118 held in filter holder 119. Filter holder 119 is slidably received in an imaging aperture through stage 112 and may be slidably removed from the imaging aperture of stage 112 along path 121. Path 121 does not pass through the imaging device position, which allows the filter holder to be removed or inserted without disturbing an imaging device in the imaging device position.

In some embodiments, the smartphone-based imaging platform further includes at least one thumb-screw stage-adjuster governing the vertical translation of the stage relative the sample mount. In some embodiments, the stage is mounted to the housing using one or more threaded fasteners each passing through the stage and received in a surface of the housing, the position of the stage adjustable within bounds defined by the size of the threaded fasteners. Imaging platform 100 includes two spring-loaded thumbscrews 116 which operate as a focusing mechanism to raise and lower the smartphone 102 relative the sample position.

In some embodiments, the imaging housing encloses the sample position and the laser source within a housing interior formed by a set of sidewalls overlaid by the stage, the stage including an imaging aperture through which the smartphone position directs the camera. In some embodiments, one or more components of the imaging platform may be 3D-printed. For example, one or more of the stage, the sample mount, and the sidewalls of the housing may be 3D-printed. Imaging platform 100 includes sidewalls 122 which substantially encompass the sample position and are overlaid by stage 112 to form an enclosed space when housing 103 is placed on a flat surface. The space enclosed by housing 104 is protected by sidewalls 122 and stage 112, which may reduce interference or light contamination.

In some embodiments, the intensity of the laser source is adjustable by modifying the power supply, such as by use of a rheostat coupled between the laser source and the smartphone. Imaging platform 100 includes a rheostat 124 coupled between the smartphone 102 and the laser source 106. A circuit diagram for rheostat 124 is shown in FIG. 7.

In some embodiments, the smartphone-based imaging platform further includes at least one laser dial coupled to the laser source to adjust an angle of the laser and a distance between the laser source and the sample position. For example, a manual focusing knob may be secured to a sidewall of the housing and coupled to the laser source or the beam-shaping lens to control the position of the laser source or the beam-shaping lens. In some embodiments, the laser or beam-shaping lens is repositionable within the housing relative the sample position. Imaging platform 100 includes knob 125 coupled to laser source 106 to adjust the position and angle of laser source 106. Knob 125 may be manipulated by turning or withdrawing the knob, each action controlling one of the laser position and the laser angle.

In some embodiments, target materials, which are isolated by magnetic pull-down after the composite materials bind to target antigens via antibodies, are pipetted into a chamber slide for cell counting, the chamber slide provided to the imaging platform, illuminated by the laser, and the fluorescence imaged by the imaging device camera. In some embodiments, the targets are then counted in software, such as a program identifying and counting areas of high intensity on an image. In some embodiments, commonly-available smartphone cameras are sufficiently sensitive due to the brightness of the composite materials of the present application.

The following non-limiting example is illustrative of the present application:

EXAMPLES

Materials and Methods

Materials

Dextran RapidSpheres (dextran-coated magnetic iron oxide nanoparticles; MNPs) and the Do-It-Yourself Positive Selection Kit II (for formation of tetrameric antibody complexes) were from STEMCELL Technologies (Vancouver, BC, Canada). Anti-HER2 antibody (NBP2-32863) was from Novus Biologicals (Centennial, CO). Carbon-coated copper grids (300 mesh) were from Ted Pella (Redding, CA). CdSe/CdS/ZnS QDs (QD575, QD605, QD635) were synthesized using standard methods (Yu, W. W.; Peng, X. Angew. Chemie—Int. Ed. 2002, 41 (13), 2368-2371; Li, J. J. et al. J. Am. Chem. Soc. 2003, 125 (41), 12567-12575). CdZnSe/CdZnS/ZnS QDs (QD485) were synthesized using the method of Susumu, K. et al. (Chem. Mater. 2017, 29 (17), 7330-7344). The notations are of the form QDA, where A is the wavelength of peak PL emission. Borate buffer was 50 mM, pH 9.3. The primary buffer (denoted as separation buffer) used for live-cell studies was PBS buffer supplemented with 2% fetal bovine serum (v/v) and 1 mM EDTA. PBS buffer was from Gibco Life Technologies. The composition of the primary PBS buffer used was pH 7.2, 1.54 mM $KH_2PO_4$, 2.71 mM $Na_2HPO_4$, 155 mM NaCl, and is denoted as PBS.

Dextran (*Leuconostoc mesenteroides*, 9000-11000 Da MW or *Leuconostoc* spp. ~6000 Da MW) (6 kDa dextran was used only for the experiments in FIG. 4), sodium (meta)periodate, 1-(3-aminopropyl)imidazole (API), sodium cyanoborohydride, epichlorohydrin, sodium borohydride, L-Histidine (His), tetramethyl ammonium hydroxide (TMAH), and reduced L-Glutathione (GSH) were from Sigma-Aldrich (Oakville, ON, Canada). Boric acid and ethylenediaminetetraacetic acid (EDTA) were from Fisher Scientific (Toronto, ON, Canada). Sodium tetraborate decahydrate, potassium carbonate, and sodium bicarbonate were from Amresco (Solon, OH). Dialysis membrane (3.5 kDa MWCO) was from Spectrum Laboratories (Rancho Dominguez, CA). Deionized water was from a MilliQ Synthesis water purification system (Millipore, Burlington, MA). Borate buffer was 50 mM at pH 9.3.

Smartphone-Based Imaging Platform

The smartphone imaging platform was designed using AutoCAD 2017 AutoDesk Student 3-D drafting software (AutoDesk, San Rafael, CA), and the components were 3-D printed on a 5th generation MakerBot Replicator 3-D Printer (MakerBot, Brooklyn, NY) using black PLA filament (MakerBot). A Galaxy S7 smartphone (Samsung, Suwon, South Korea) and the Camera FV-5 Pro app (Version 3.31.4; FGAE Studios, Stuttgart, Germany) were used for imaging. A D405-20 laser diode (405 nm, 20 mW, 5V 75 mA Radial, Can, 3 Lead, 5.6 mm, TO-18) from US-Lasers Inc. (Baldwin Park, CA) was used as the excitation source. Cell counting chamber slides (Countess, C10283) were from Invitrogen (Carlsbad, CA). Optical components were from Thorlabs Inc. (Newton, NJ).

The divergence of the beam from the as-received 405-nm laser diode needed to be adjusted for optimal sample illumination. FIG. 6 shows the optics that were used for this purpose. The highly divergent beam from the laser diode was brought to a low convergence angle through two initial lenses and then further adjusted to the desired angle of divergence with a third lens. The final beam illuminated the sample chamber with satisfactory intensity and uniformity. The laser intensity was adjusted by a rheostat for which the circuit diagram is shown in FIG. 7.

Preparation of API-Modified Dextran (API-Dex)

FIG. 8 summarizes the preparation of API-modified dextran. The protocol is for 10 kDa dextran but is readily adapted to 6 kDa dextran.

Dextran (1, 0.50 g, ~10 kDa MW, ~50 μmol of polymer chains or ~3.1 mmol anhydroglucose) was weighed into a 40-mL glass vial and dissolved in 20 mL deionized water. An aliquot of 0.1 M $NaIO_4$ (3.1 mL, 0.31 mmol, 0.1 equiv.) was added and the sample was covered in foil and mixed at 4° C. for 8-12 h (overnight). The samples were then dialyzed against 1.0 L of deionized water using 3.5 kDa-MWCO dialysis tubing for 2×~24 h periods with one water change in between. The purified samples were freeze-dried to yield a fluffy white solid of oxidized dextran (3, Ox-Dex).

Ox-Dex (3, 0.10 g, 0.617 mmol anhydroglucose, maximum 0.123 mmol aldehyde if 100% efficiency in the preceding step) was added to a 5-mL glass vial and dissolved in 2 mL of deionized water. Neat 1-(3-aminopropyl)imidazole (API, 2; 19.7 μL, 0.165 mmol, 1.3 equiv.) was added and the solution was mixed at room temperature for 2 h. Next, an aliquot of $NaCNBH_3$ (aq) (0.25 mL of 51 mg/mL in deionized water) was added to the reaction, which was then left to mix overnight at room temperature. The final reaction mixture was pipetted into 95% ethanol (20 mL) to precipitate the dextran, which was then pelleted via centrifugation at 13 000 rcf for 5 min. The supernatant was removed, the pellet re-dissolved in 2 mL of deionized water, and re-precipitated with ethanol followed by centrifugation to collect the pellet of API-modified dextran (4, API-Dex). The pellet was dried under reduced pressure to yield an off-white powder.

Preparation of MNP@QD

Dextran coated MNPs (an example of a polymer-coated colloid core) were stabilized by crosslinking the dextran in a 7.7% (v/v) solution of epichlorohydrin in 1M NaOH for 24 h. The nanoparticles were washed and resuspended in MilliQ water. The dextran coating was then oxidized in 1 mM $NaIO_4$ for 1 h in the dark. The oxidized nanoparticles were washed and resuspended in deionized water and then coupled with 100 mM 1-(3-aminopropyl)imidazole (API) via reductive amination in 12 mM $NaBH_4$ (aq). The nanoparticles were then washed and resuspended in borate buffer. All steps to this point were done at room temperature. The API-functionalized MNPs were then self-assembled with aqueous ligand-stabilized QDs (histidine, glutathione, or CL4 ligands) via sonication for 15 min in a water bath set at 30° C. Unbound QDs were separated from the resulting MNP@QD assemblies by magnetic pelleting and washing. The MNP@QD were then overcoated with API-Dex at 60° C. (see below). Excess API-Dex was removed by magnetic pelleting and washing. The MNP@QD were then stored at 4° C. until needed. See below for further details regarding preparation of the particle assemblies and still further below for methods for the characterization of the MNP@QD.

Epichlorohydrin-crosslinked MNP (X-MNP). Dextran-coated magnetic nanoparticles (MNP, 2.8 nM in water; 800 µL) were pipetted into a 5-mL glass vial. The MNPs were magnetically pelleted and the supernatant was removed by pipette. A 1.28 mL solution of 7.7% (v/v) epichlorohydrin was prepared in 1 M NaOH and the pelleted MNPs were resuspended in the epichlorohydrin solution. The vial was sealed and kept in the dark as it incubated for 24 h on a shaker at room temperature. The resulting X-MNP pelleted magnetically, and the epichlorohydrin solution was removed via pipette. The X-MNP were resuspended in 1 mL of deionized water, subsequently pelleted, and the supernatant removed. The resuspension and pelleting steps were repeated for a total of five washes to remove excess epichlorohydrin. After the final wash, the X-MNPs were resuspended in 1.28 mL of deionized water and used in the next step.

Oxidized X-MNP (Ox-MNP). A 125 mM solution of NaIO4 (aq) was prepared by dissolving ~27 mg NaIO4 in 1.0 mL deionized water. An aliquot (10.24 µL) of $NaIO_4$ (aq) was added to 1.28 mL of X-MNP in water (final concentration of ~1.0 mM $NaIO_4$). The sample was mixed via pipette and kept sealed and protected from light while mixing on a shaker at room temperature for 1 h. The Ox-MNP were pelleted and washed with 3×1 mL volumes of borate buffer. After the final wash, the Ox-MNP were resuspended in 1.28 mL of borate buffer and were used in the next step.

1-(3-aminopropyl)imidazole-modified MNP (API-MNP). Ox-MNP were pelleted using a magnet and then resuspended in 1.28 mL of a 100 mM solution of 1-(3-aminopropyl)imidazole (API) in borate buffer. The sample was sealed and kept in the dark as it incubated overnight at 4° C. Next, 64 µL of 0.25M (10 mg/mL) $NaBH_4$ in 0.5 M sodium bicarbonate (pH 10.5) was added to the reaction mixture. The sample was mixed in the dark for 20 min. Following mixing, the API-MNPs were pelleted using a magnetic and washed with 5×1 mL volumes of borate buffer. After the final wash, the pellet was resuspended in 1.28 mL of borate buffer.

Ligand exchange of QDs. L-Histidine-coated QDs (His-QDs) were prepared by weighing 100 mg of L-histidine (0.645 mmol) into a 1.7-mL microcentrifuge tube. The L-histidine was dissolved in 300 µL tetramethylammonium hydroxide solution (TMAH; 25 wt % in methanol). As-synthesized hydrophobic QDs in organic solvent (20 µL aliquot; concentration on the order of 102 µM) were transferred into a second 1.7-mL microcentrifuge tube, then diluted to 900 µL with $CHCl_3$. The L-histidine solution was then added to the hydrophobic QD solution and the sample was mixed by vortex. The sample was kept in the dark and incubated at room temperature for 1 h. Following incubation, a biphasic extraction was performed by adding 200 µL of borate buffer to the reaction mixture, into which the His-QDs dispersed. The aqueous phase was isolated and excess TMAH was removed by precipitating the QDs with absolute ethanol (~600 µL) and centrifugation at 4800 rcf for 5 min. The supernatant was then removed and the His-QDs were redispersed in 100 µL of borate buffer. After three cycles of precipitation and washing, the His-QDs were dispersed in 200 µL borate buffer and stored at 4° C. until needed.

Ligand exchange with glutathione (GSH; to prepare GSH-QDs) was done analogously to the ligand exchange with L-histidine. Ligand exchange with CL4 was done as described previously (Susumu, K. et al. J. Am. Chem. Soc. 2011, 133 (24), 9480-9496; Susumu, K. et al. Chem. Mater. 2017, 29 (17), 7330-7344).

Self-assembly of MNP@QD. API-MNs (450 µM, 20 µL in borate buffer) were pipetted into a 1.7 mL-microcentrifuge tube and QDs (20 µL, 29 µM) were added. (The QDs were His-QDs, except for the experiments in FIGS. 3B and 16-18, which were GSH-QDs, and FIG. 4, which were CL4-QD485.) The samples were sonicated in a water bath at 30° C. for 15 min. After sonication, the MNP@QDs were pelleted magnetically over a period of 2-3 min. Excess QDs in the supernatant were then removed via pipette and the pellet was washed with carbonate buffer (100 µL, 0.1M, pH 9.3). The MNP@QD pellet was then resuspended in 20 µL carbonate buffer and sonicated briefly to break up any large aggregates.

Overcoating MNP@QD with API-modified Dextran. MNP@QDs were overcoated with API-modified dextran (API-Dex; vide supra) to further stabilize the assemblies and to provide a handle for conjugation with TAC. A solution of API-Dex (25 mg/mL) was prepared in 0.1 M carbonate buffer (pH 9.3) and a 100 µL-volume was transferred into a 1.7-mL microcentrifuge tube. MNP@QD (450 µM, 20 µL) were then added to this solution. The sample was briefly vortexed and sonicated, then incubated at 60° C. for 15 min. The overcoated MNP@QD were then pelleted magnetically over a period of 2-3 min, and the supernatant was removed via pipette. The pellet was washed with carbonate buffer (100 µL) and then resuspended in carbonate buffer (40 µL).

MNP@QD Characterization

Transmission electron microscope (TEM) images were acquired using a Hitachi High-Technologies H7600 (Tokyo, Japan). Samples were imaged at an accelerating voltage of 100 kV and were prepared by drop-casting 2×0.5 µL of ~1 µM solution of nanoparticles (diluted in deionized water) on a TEM grid with drying in a dark box overnight. Scanning electron microscope (SEM) imaging and energy-dispersive X-ray (EDX) analysis were done on a Helios NanoLab 650 Focused Ion Beam system (FEI/Thermo Fisher Scientific, Hillsboro, OR). The samples were prepared by drop-casting on TEM grids. Imaging was done at 2 kV/50 pA for secondary electron mode, and 2 kV/0.20 nA for backscattered electron mode. An accelerating voltage of either 5 kV or 10 kV was used for EDX analysis.

X-ray photoelectron spectroscopy (XPS) was done on a Leybold MAX200 XPS spectrometer (Cologne, Germany) via a survey scan for binding energies between 0 to 1075 eV. The samples were prepared by drop-casting onto acid-washed circular glass slides and allowed to dry overnight in the dark. Sample volumes and concentrations: MNP (5 μL, 1.79 nM), API-MNP (20 μL, 331 μM), MNP@QD605 (15 μL, 331 μM, no API-Dex overcoating).

Attenuated total reflectance infrared spectroscopy (ATR-IR) was done on a Perkin Elmer Frontier FT-IR Spectrometer (Waltham, USA) with a ZnSe ATR crystal. Transmittance was measured between 525 and 4000 cm$^{-1}$ with averaging over 8 scans. MNP, API-MNP, and MNP@QD605 (post-purification) samples were prepared by adding absolute ethanol (via micropipette) to 10 μL of nanoparticles until the samples flocculated. The flocculated material was then pelleted via magnet, the supernatant was removed, and the samples were resuspended in 30 μL of dichloromethane. Samples were pipetted directly onto the ATR-IR crystal and dried in air before taking measurements.

The hydrodynamic size and concentration of the MNP and MNP@QD samples were determined on a NS300 Nanoparticle Tracking Analyzer (Malvern Instruments, Malvern, UK) instrument equipped with a 488 nm peak wavelength laser, operating at a maximum power of 45 mW. Measurements were done in both scattering mode and fluorescence mode (500 nm longpass filter). Samples were prepared by diluting 200-500 fold in deionized water to a total volume of ~1 mL.

Fluorescence Microscopy

Some characterization experiments made use of imaging on a research-grade fluorescence microscope. This microscope was an IX83 inverted microscope (Olympus, Richmond Hill, ON, Canada) equipped with an X-Cite 120XL metal-halide light source (Excelitas Technologies, Mississauga, ON, Canada), a white-LED transmitted light source, an Orca-Flash 4.0 V2 sCMOS camera (C11440; Hamamatsu Photonics, Hamamatsu, SZK, Japan), motorized filter wheels (Sutter Instruments, Novato, CA, USA), and Meta-Morph/MetaFluor software (Molecular Devices, Sunnyvale, CA). Filters and dichroic mirrors were from Chroma (Bellows Falls, VT).

TAC Anti-HER2 Complexes

A 15 μg/mL stock solution of TAC with anti-HER2 antibody was prepared in PBS buffer by following the manufacturer's protocol for the Do-It-Yourself Positive Selection Kit II. The sample was incubated overnight at 37° C. After overnight incubation, the TAC-anti-HER2 complex was diluted to 1 mL with PBS buffer and stored at 4° C. until needed.

Cell Culture

SK-BR3 cells (ATCC HTB-30 Manassas, VA, USA), a human breast cancer cell line, were cultured in a humidified incubator with 95% air/5% CO$_2$ at 37° C. The culture medium was McCoy's 5A (GE Healthcare, Chicago, IL) supplemented with 10% v/v fetal bovine serum and 1× antibiotic and antimycotic (ThermoFisher, Waltham, MA). Cells were cultured in T25 flasks and sub-cultured every 5-7 days.

MDA-MB-231 cells (ATCC HTB-26 Manassas, VA, USA), a human epithelial breast cancer cell line, were cultured analogously to the SK-BR3 cells; however, the culture medium was Dulbecco's Modified Eagle Medium (DMEM) (Sigma Aldrich) supplemented with 10% v/v fetal bovine serum, 1× antibiotic and antimycotic (ThermoFisher, Waltham, MA, USA), 2 mM L-glutamine (Gibco, 25030081), and 0.1 mM MEM non-essential amino acids (Gibco, 11140-050).

Cell-Counting Assay

For live-cell counting assays, cultured SK-BR3 cells (HER2 positive) were harvested, counted using a commercial instrument (Countess II Cell Counter; Invitrogen), then diluted and spiked into separation buffer at the desired concentration. MDA-MB-231 cells (HER2 negative) were similarly spiked into select samples alongside the SK-BR3 cells. TAC with anti-HER2 and MNP@QD were added in sequence to the cell suspension, which then stood at room temperature for 5 min. A permanent magnet was applied to collect the MNP@QD and any bound cells as a pellet. The supernatant was removed, the pellet washed once with separation buffer, and the pellet resuspended in separation buffer. A 10 μL aliquot was then transferred to a chamber slide for imaging on the SIP. Details of the cell culture, harvesting, fixation procedures, and cell-counting image analysis algorithm are described in detail below.

Counting DAPI-stained cells on the SIP. Cultured SK-BR3 cells were trypsinized, centrifuged, and then fixed in ice-cold ethanol for 15 min. The cells were pelleted via centrifugation at 85 rcf for 5 min and the supernatant was removed. The cells were resuspended in fresh PBS buffer and rehydrated for 15 min. The cells were centrifuged at 85 rcf for 5 min and the supernatant was discarded. The cell pellet was resuspended in a solution of 4',6-diamidino-2-phenylindole (DAPI; 2 mL, 2.9 μM) and incubated in the dark for 10 min at room temperature. Following incubation, the cells were pelleted via centrifugation, and the supernatant was removed. The cell pellet was then resuspended in 2 mL of fresh PBS buffer. The average concentration of cells (measured in triplicate using a Countess II cell counter was 5.5×10$^6$ cells/mL. Triplicate samples with dilution factors ranging from 1.4-fold to 10 000-fold were prepared in 1.7-mL microcentrifuge tubes by dilution with fresh PBS buffer. Each sample was pipetted into a chamber slide and imaged on the SIP. The acquired images were further processed on ImageJ and the cells were counted. The same samples were also counted on the Countess II cell counter (vide supra) for validation. This procedure was used to generate the data in FIG. 11.

Counting and imaging fixed SK-BR3 cells labeled with MNP@QDs. This procedure was used to generate the data in FIGS. 4 and 18. A suspension of freshly trypsinized SK-BR3 cells (~10$^6$ cells) was pelleted by centrifugation at 55 rcf for 5 min. The supernatant was removed and the pellet resuspended in 2 mL of PBS buffer. A volume of 2 mL of 4% (w/v) paraformaldehyde in PBS was added and the sample gently mixed via pipette. The sample was incubated at room temperature for 5-10 min before pelleting via centrifugation at 55 rcf for 5 min. The supernatant was discarded and the pellet resuspended in 4 mL of PBS buffer.

For each color of MNP@QD, 10 μL of paraformaldehyde-fixed SK-BR3 cells (in PBS) was pipetted into a 1.7 mL microcentrifuge tube. The SK-BR3 cell suspension was then spiked with pre-formed TAC with anti-Her2 (1 μL, 97 fmol), followed by MNP@QD (2 μL, 1.3 fmol, ~8×10$^8$ assemblies). The sample mixture was mixed briefly via pipette and then incubated on the benchtop for 5 min. Following incubation, the labeled cells were pelleted magnetically and the supernatant removed by pipette. The cells were resuspended in 20 μL of fresh PBS buffer.

For imaging on the SIP, 10 μL of the labeled cell suspension was pipetted into a chamber slide. For research-grade fluorescence microscope imaging, samples were prepared by pipetting 7.5 µL of a suspension of labeled cells onto a microscope slide. A cover slip was applied, and then the sample was inverted and imaged through the cover slip. The fluorescence filter sets used were as listed in Table 3. The emission spectra of the cells labeled with MNP@QD485 and MNP@QD575 were acquired with a diode-array spectrometer (Greenwave 16 VIS-50; StellarNet, Tampa, FL) that was coupled to the trinocular head of the microscope via a fiber-optic cable. ImageJ software was used for processing images.

TABLE 3

Fluorescence microscopy optics for SK-BR3 labeling.

| Label | Exc. Filter [a] | Em. Filter [a, b] | Dichroic Mirror [c] | Objective Lens [d] |
|---|---|---|---|---|
| MNP@QD485 | 405/20 BP | 460/50 BP* | T425 | 100 XO |
| MNP@QD575 | 405/20 BP | 550 LP | T510 | 100 XO |
| MNP@QD605 | 405/20 BP | 600 LP | T590 | 100 XO |
| MNP@QD635 | 405/20 BP | 600 LP | T590 | 60 X |

Notes:
[a] Center wavelength/bandwidth, BP = bandpass filter.
[b] LP = longpass filter.
[c] T = transmission cut-on wavelength. All numbers in units of nanometers.
[d] X = magnification factor, air-immersion; XO = magnification factor, oil-immersion.

Counting live SK-BR3 cells on the SIP. The following describes the procedures used to generate the data in FIG. 5. For all counting assays, the mean numbers of cells spiked into samples were estimated from triplicate measurements of 10-µL aliquots of each stock cell suspension using Countess Chamber Slides and a Countess II Cell Counter as per the manufacturer's protocol.

Counting increasing numbers of SK-BR3 cells without MDA-MB-231 cells. The following procedure was used to generate the data in FIG. 5B. Cultured SK-BR3 cells were trypsinized, centrifuged, and resuspended in separation buffer. Three stock suspensions of SK-BR3 cells with concentrations of ~8 700, ~100 200, and ~570 300 cells/mL were prepared in separation buffer. For validation and determination of recovery percentages, the number of cells per sample was measured by pipetting an aliquot (10 µL) into a chamber slide for counting on a Countess II cell counter.

Samples were prepared in triplicate with the following numbers of SK-BR3 cells spiked into 1.7 mL microcentrifuge tubes as 10 µL aliquots: ~90, ~500, ~750, ~1000, ~2850, ~5700, and ~57 000 cells. The 90-cell sample was prepared from the 8700-cell stock suspension. The 500-, 750-, and 1000-cell samples were prepared from the 100 200-cell stock suspension. The 2850-, 5700-, and 57 000-cell samples were prepared from the 570 300-cell stock suspension.

Next, a spike of TAC with anti-HER2 (1 µL, 97 fmol) was added to the samples, followed by a spike of MNP@QD605 (2 µL, 1.3 fmol, ~8×10⁸ assemblies). The samples were mixed via pipette and then left on the benchtop at room temperature for 5 min. The labeled cells were pelleted magnetically and the supernatant was removed. The cell pellet was washed with separation buffer (20 µL), and the cells were resuspended in fresh separation buffer (20 µL). An aliquot of each sample (10 µL) was then pipetted into a chamber slide and imaged on the SIP.

Counting increasing numbers of SK-BR3 cells with a constant number of MDA-MB-231 cells. The following procedure was used to generate the data in FIG. 5C. Separately, SK-BR3 and MDA-MB-231 cells were trypsinized, centrifuged, and resuspended in separation buffer. The MDA-MB-231 cell suspension was diluted to a concentration of ~1 230 000 cells/mL. Three stock suspensions of SK-BR3 containing mean concentrations of ~16 700, ~167 000, ~484 000, and ~1 180 000 cells/mL were prepared in separation buffer. For validation and determination of recovery percentages, the number of cells per sample was measured by pipetting an aliquot (10 µL) into a chamber slide for counting on a Countess II cell counter.

Samples were prepared in triplicate with the following numbers of SK-BR3 cells spiked into 1.7 mL microcentrifuge tubes as 10 µL aliquots: ~167, ~1 670, ~4 840, ~5 890, and ~11 800. Next, ~6 140 MDA-MB-231 cells were added into each sample. The 167-cell spiked sample was prepared from the 16 733 cell/mL stock suspension. The 1 673-cell sample was prepared from the 167 333 cell/mL stock suspension. The 4 840-cell sample was prepared from the 484 000 cell/mL stock suspension. The 5 892- and 11 783-cell samples were prepared with the 1 180 000 cell/mL stock suspension.

Next, a spike of TAC with anti-HER2 (1 µL, 81 fmol) was added to the samples, followed by a spike of MNP@QD635 (2 µL, 1.3 fmol, ~8×10⁸ assemblies). The samples were mixed via pipette and then left on the benchtop at room temperature for 5 min. Following incubation, the labeled cells were pelleted magnetically and the supernatant was removed. The cell pellet was washed with separation buffer (20 µL) and the cells were resuspended in fresh separation buffer (20 µL). An aliquot (10 µL) of each sample was then pipetted into a chamber slide and imaged on the SIP.

Counting a constant number of SK-BR3 cells with an increasing number of MDA-MB-231 cells. The following procedure was used to generate the data in FIG. 5D. Separately, SK-BR3 and MDA-MB-231 cells were trypsinized, centrifuged, and resuspended in separation buffer.

Three samples were prepared in triplicate by pipetting 5 µL of ~895 000 cell/mL stock of SK-BR3 cells into 1.7 mL Eppendorf tubes. The samples were then spiked with 10 µL of separation buffer, 858 000 cell/mL MDA-MB-231 stock, or 84 000 cell/mL MDA-MB-231 stock.

Next, a spike of TAC with anti-Her2 (1 µL, 97 fmol) was added to the samples, followed by a spike of MNP@QD575 (2 µL, 1.3 fmol, 8×10⁸ assemblies). The samples were mixed via pipette and then incubated on the benchtop at room temperature for 5 min. Following incubation, the labeled cells were pelleted magnetically and the supernatant containing unlabeled cells (MDA-MB-231), was removed. The cell pellet was then washed with 20 µL separation buffer and the cells were resuspended in 20 µL of fresh separation buffer. An aliquot (10 µL) of each sample was then pipetted into a chamber slide and imaged on the SIP.

Image Analysis for Cell Counting

Although the total image field of view from the SIP was 79 mm², a 2×3 mm² area was analyzed for cell counting. This area is similar to the 2×2 mm² area used by the commercial Countess II cell counter. It should be noted that the chamber slide in the SIP can be translated to allow multiple 2×3 mm² areas to be imaged and analyzed for better counting statistics, which was done for live cell assays. This feature is particularly useful for low cell concentrations where it may be necessary to search for cells (e.g. less than one cell per field of view).

Once an image was acquired, the background was subtracted using ImageJ, using the subtract background function, with a rolling ball radius of 12. An example is shown in FIG. 9.

Background-subtracted images were analyzed in ImageJ using the analyze particles function, as summarized in FIG.

10. This function allows for objects within a certain size and shape range to be defined as particles (i.e. individual cells in the present system). The isolated cells were approximately spherical in shape when suspended in solution and have a relatively well-defined size range, which facilitated reliable counting of cells with exclusion of dust and debris, nanoparticle aggregates, or other objects in the field of view. Alternately, the use of ImageJ may be replaced with a custom-coded smartphone app for these or equivalent functions.

Results & Discussion

Smartphone-Based Imaging Platform

Figure 27:
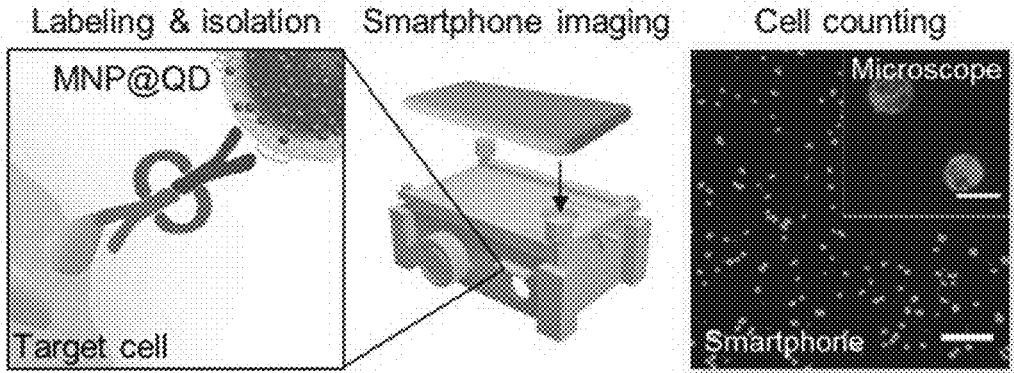
FIG. 27 shows a rendering of an exemplary smartphone-based fluorescent cell imaging platform (SIP).

FIG. 2A shows a rendition of the SIP 100 (see also FIG. 27), which was manufactured by 3-D printing. The SIP includes a smartphone 102 (FIG. 2C), a housing 104 (FIG. 2A), and laser source 106 (FIG. 2B). The housing 104 includes a sample mount 108 (FIG. 2D) for holding a sample, sample mount 108 configured to hold a chamber slide containing the sample. The housing 104 also includes an imaging device mount 110. Imaging device mount 110 forms a top cover of the SIP as stage 112 with a recess 114 in a top surface thereof that aligns the smartphone camera with additional optics situated in the lid. This top-stage is manually translated along the vertical axis 115 via two spring-loaded thumbscrews 116 which operate as a focusing mechanism. The optics, illustrated in FIG. 2B, included a 500 nm long-pass emission filter 118 and two half-inch magnifying lenses 120 (f=15 mm bi-convex; f=19 mm achromatic doublet). The optics provided an imaging field-of-view of 10.5×7.9 $mm^2$, corresponding to an image pixel size of ~2.6 μm. Cells were counted in a smaller area of the image, 2×3 $mm^2$, where excitation (vide infra) was most uniform and imaging aberrations were at a minimum. The emission filter 118 is received in an imaging aperture through the stage, and sits in a holder that slides in and out (without moving the smartphone) for quick changes of filters to match the emitter of interest. Housing 104 also includes a set of sidewalls 122 surrounding the sample position and the laser source.

The excitation source in the SIP was a 20-mW violet (405 nm) laser diode, which is both a common and ideal excitation wavelength for QDs (Algar, W. R. et al. Anal. Chem. 2011, 83 (23), 8826-8837; Algar, W. R.; Krull, U. J. Sensors 2011, 11 (6), 6214-6236). The laser output was shaped through a series of lenses (see FIG. 6) to illuminate a narrow section of the sample from below. A dial 124 translated the laser in the lateral direction and adjusted the angle of the beam. The laser was powered through the microUSB port of the smartphone and its intensity was manually adjusted via a rheostat 126 (see FIG. 7).

The sample (as a cell suspension) was loaded into commercially available cell-counting slides that had two plastic chambers, each 17×6 $mm^2$ in area and 0.1 mm high, holding a sample volume of ~10 μL. The volume of the section of the image where cells were counted was ~0.6 μL. Each slide was useful for two cell-counting measurements, which were validated on the SIP by imaging fixed SK-BR3 breast cancer cells stained with 4',6-diamidino-2-phenylindole (DAPI). This nuclear stain was chosen for validation because it provided high signal-to-noise ratios (10±6 as ±standard deviation, SD) and was adequately excited by the SIP laser diode. Dilutions of fixed cells with concentrations between $5.5\times10^2$ and $5.5\times10^6$ cells/mL were counted on the SIP and, in parallel, on a commercial instrument (Countess II Cell Counter). A near 1:1 correlation between the two measured concentrations was observed (see FIG. 11, slope=1.01, correlation coefficient $R^2$=0.996).

Composite MNP@QD Nanoparticles

To enable concurrent magnetic isolation and fluorescent labeling of cells, a composite particle (MNP@QDs) was developed. The dextran coating of commercially available MNPs were chemically modified with API for self-assembly with ligand-stabilized QDs. The QDs were generally coated with either glutathione (GSH) or histidine (His) ligands, although it was possible to assemble QDs coated with other ligands as well (e.g. zwitterionic compact ligand CL4). The API-modification was beneficial for efficiently assembling aqueous QDs to the MNPs, as these particles retained ~180-fold more QDs than unmodified MNPs (measured by brightness, see FIG. 12 for details). Although there is batch-to-batch variation, the number of QDs assembled per API-modified MNP (API-MNP) was estimated to be 1000±400 for QD635 and 9200±3600 for QD575 (see FIG. 13 for details). In a final step, the MNP@QD assemblies were over-coated with API-modified dextran (API-Dex). MNP@QDs that were not over-coated with API-Dex or mixed with unmodified dextran quickly flocculated out of solution. In contrast, MNP@QD mixed with API-Dex remained as an optically clear solution, indicative of colloidal stability from the API-mediated functionalization (see FIG. 15). The API-Dex was also useful for conjugation of the cell-targeting antibody (vide infra).

Figures 3A, 3B, 3C, 3D, 3E, 3F, 3G:
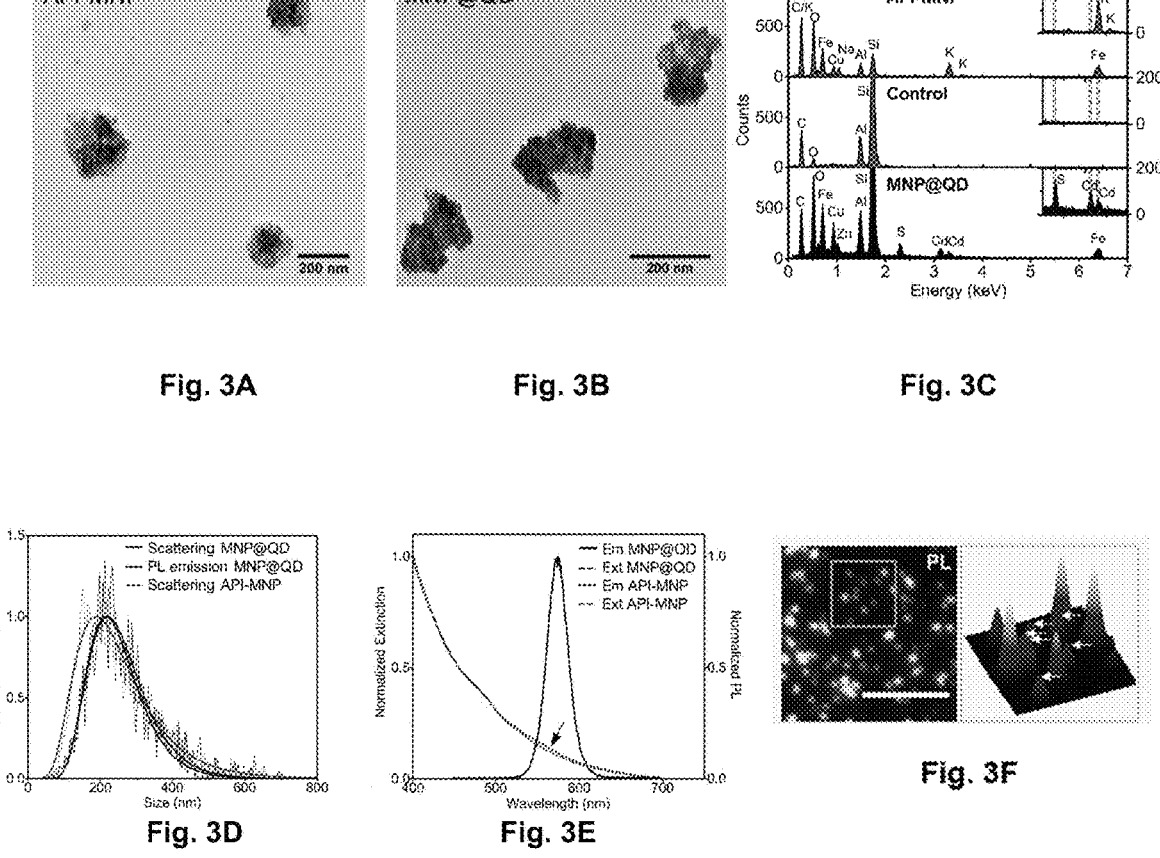
FIG. 3A shows TEM images of an exemplary 1-(3-aminopropyl)imidazole (API)-MNP.
FIG. 3B shows TEM images of exemplary MNP@QD605 (9.8±1.3 nm diameter for QD605).
FIG. 3C shows EDX analysis of exemplary API-MNP, MNP@QD, and sample substrate (control). Inset graphs represent the 2-4 keV range. Vertical dotted lines in the inset align with S and Cd peaks.
FIG. 3D shows exemplary API-MNP and MNP@QD575 size distributions (252±117 nm, 250±81 nm) determined by NTA. The API-MNP had no measurable PL emission.
FIG. 3E shows UV-visible extinction (Ext) and PL emission (Em) spectra for exemplary API-MNP and MNP@QD575. The arrow highlights the first exciton peak of the QD575.
FIG. 3F shows a fluorescence microscopy image of exemplary MNP@QD575 (left; scale bar=5 μm). A three-dimensional pixel-intensity plot for the boxed area of the image is provided (right). Single MNP@QD assemblies are indicated by the white arrows.
FIG. 3G shows magnetic pelleting of exemplary MNP@QDs from a colloidal suspension.
Figure 19:
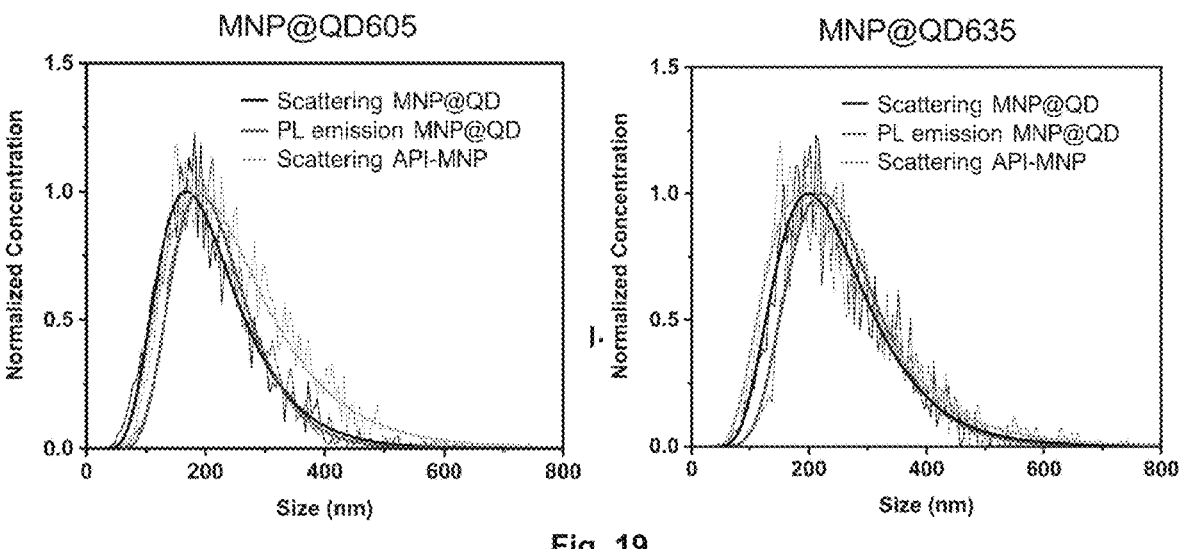
FIG. 19 shows NTA sizing data for exemplary MNP@QD605 and MNP@QD635.
Figure 20:
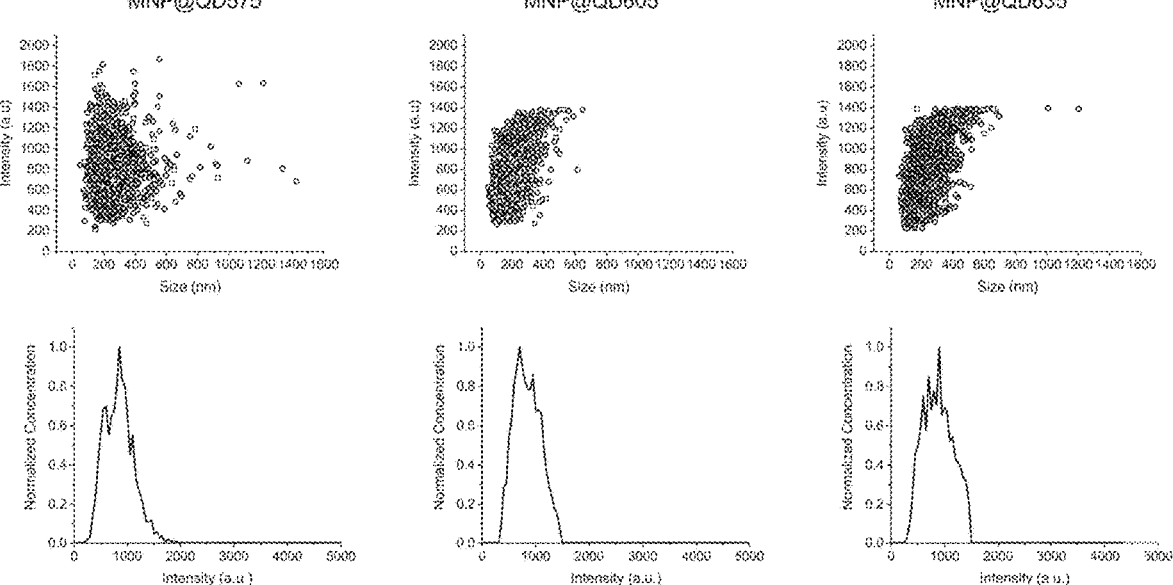
FIG. 20 shows plots of intensity versus size (top row; scatter plots) and concentration versus intensity (bottom row; histograms) for exemplary MNP@QD575, MNP@QD605 and MNP@QD635.

FIGS. 3A-B show representative transmission electron microscopy (TEM) images of API-MNP and MNP@QD. The API-MNP are non-spherical and show high-contrast iron oxide at their core. In contrast, the MNP@QD assemblies show a high density of smaller spherical dark spots across their diameter, indicative of a dense assembly of QDs. Analysis of the API-MNP and MNP@QD by scanning electron microscopy and energy-dispersive x-ray spectroscopy (SEM-EDX), FIG. 3C, shows the expected signals for the API-MNP (Fe) and QDs (Cd, Zn, S) (additional data in FIG. 16). These results were confirmed by x-ray photoelectron spectroscopy (XPS, FIG. 17). Infrared absorption data for characterization can be found in the SI (FIG. 18) and suggested that the QDs retained many of their original ligands upon assembly with the MNPs. Nanoparticle tracking analysis (NTA) was used for size analysis of the API-MNP and MNP@QD, using both scattering and PL measurement modes, although only the MNP@QDs were trackable in PL mode. FIG. 3D shows that the average size of the MNP@QD575 was 250±81 nm (±standard deviation) by scattering and 258±87 nm by PL. These values were similar to the size of the MNP by scattering (252±117 nm), although the size distribution of the API-MNP was broader. The mode size increased from 229±2 nm for the API-MNs to 238±3 nm (±standard error) for the MNP@QD, consistent with assembly of the QDs. Additional NTA characterization for MNP@QD605 and MNP@QD635 can be found in the SI (FIGS. 19-20).

The MNP@QD were also optically characterized, as shown in FIG. 3E for MNP@QD575. The UV-visible extinction spectrum of the MNP@QD575 largely resembled the scattering spectrum of the MNPs; however, the spectrum for the MNP@QD575 had a small feature at ~550 nm, which corresponded to the first exciton peak of the QD575. The PL emission spectrum of the MNP@QD575 was centered at 575 nm with a full-width-at-half-maximum of 26 nm. Other than emission spectra shifts <5 nm, the emission properties of the MNP@QD matched those of the QDs alone for all colors of QD tested. The PL excitation spectra of the MNP@QD were also consistent with the QDs alone (FIG.

21). The MNPs had no detectable PL emission. Individual MNP@QD assemblies were detectable by fluorescence microscopy, as seen in FIG. 3F, where the single assemblies were distinguished from dimers, trimers, and larger groupings by their measured intensities. The combined magnetic and PL characteristics of the MNP@QD are shown in FIG. 3G, where a colloidal solution of MNP@QD575 was quickly pelleted via a permanent magnet and long-wave UV-illumination induced bright yellow PL from the pellet.

Validation of SIP with DAPI-Stained Cells

Figure 11A:
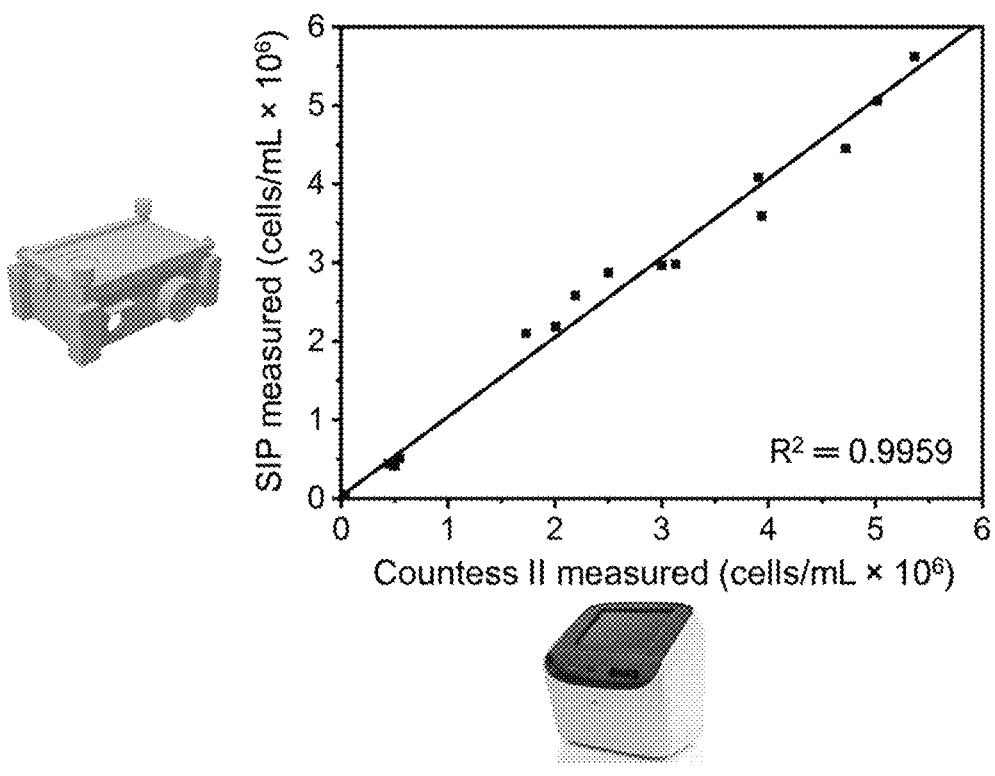
FIG. 11A shows comparison of fixed and DAPI-stained SK-BR3 cell-counting on the exemplary SIP and a commercial Countess II cell counter. The Countess II cell counter enumerates the cells by imaging the samples in brightfield mode with trypan blue dye (excluded by live cells) in solution and applying their cell-counting image analysis algorithm.
Figure 11B:
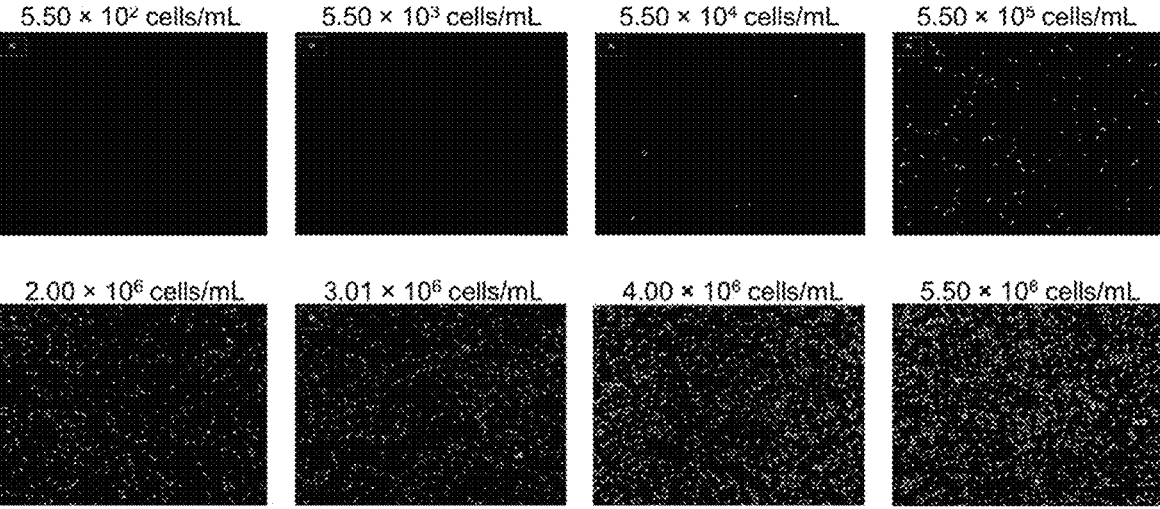
FIG. 11B shows exemplary SIP images of DAPI-stained SK-BR3 cells at various concentrations.

FIG. 11 shows the linear correlation (slope=1.01, correlation coefficient $R^2$=0.996) between the number of fixed, DAPI-stained cells counted on the SIP and those counted on the commercial Countess II cell counter. Representative images from the SIP are also shown for concentrations from $5.5 \times 10^2$ to $5.5 \times 10^6$ cells/mL. Even at low concentrations ($<10^4$ cells/mL) there are individual cells visible in a single field of view.

Benefit of API-Modification of MNPs

Figure 12A:
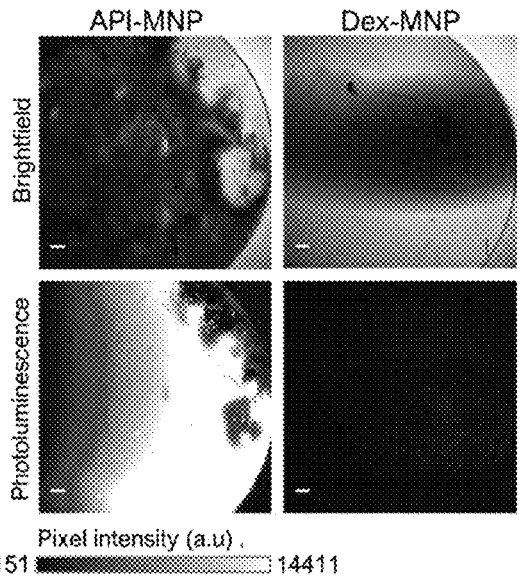
FIG. 12A shows comparison of GSH-QD605 binding to exemplary API-MNP and MNP. PL emission microscopy of exemplary API-MNP and MNP (control) after mixing with GSH-QDs. A pixel intensity bar is shown for reference. Scale bar=200 μm.
Figure 12B:
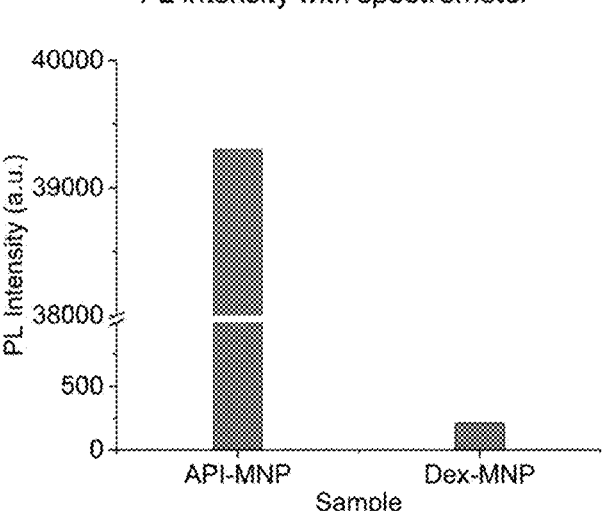
FIG. 12B shows the measured PL intensity for each sample measured on a spectrometer which was coupled to the trinocular head of the microscope.

FIG. 12 shows PL emission images of magnetically-isolated dextran-coated MNPs (i.e. as-received from supplier) and API-modified MNPs after mixing for 60 min with GSH-QD605. Integrating the total PL intensity from the nanoparticles in the image field of view (using a spectrometer coupled to the trinocular head of the microscope) indicated that the API modification resulted in ~180-fold brighter nanoparticles. This result was interpreted as ~180-fold more QDs per MNP with the API modification.

Estimating the Number of QDs Per MNP

Figure 13A:
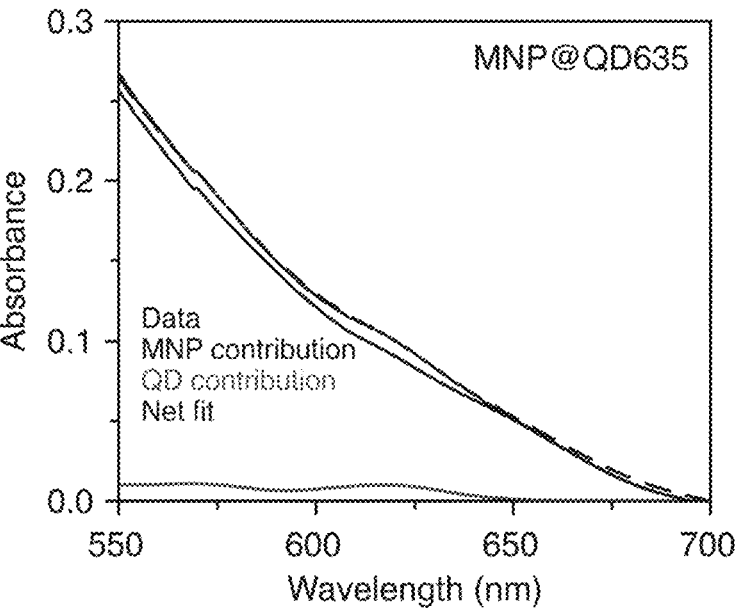
FIG. 13A shows UV-visible extinction spectra, deconvoluted contributions, and fits for estimating the number of QDs assembled per exemplary MNP for QD635.
Figure 13B:
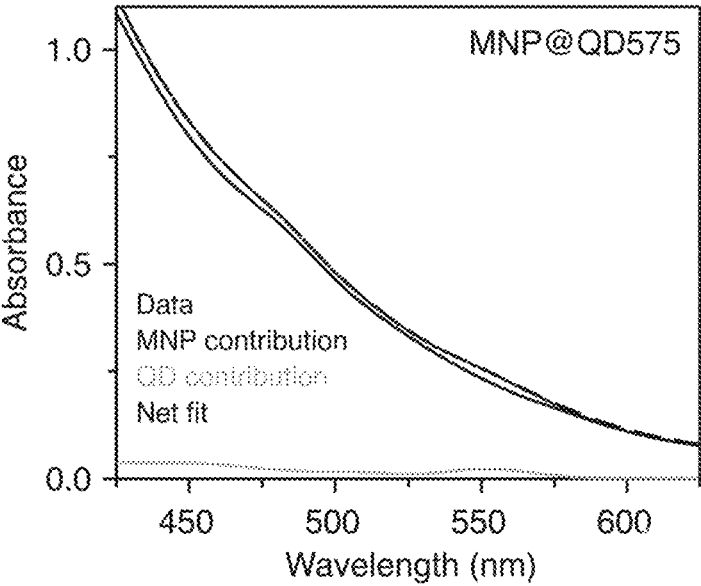
FIG. 13B shows UV-visible extinction spectra, deconvoluted contributions, and fits for estimating the number of QDs assembled per exemplary MNP for QD575.

The number of QDs per MNP was estimated by UV-visible extinction measurements of the composite NPs, bare MNPs, and QDs. A double-beam instrument was necessary to obtain adequate signal-to-noise ratios. The QD contribution to the spectra of the composite NPs was deconvoluted from the MNP scattering contribution, and the concentration of QDs was determined via the Beer-Lambert law and the absorbance at the first-exciton peak. The path length was 1 cm and the extinction coefficients were calculated from previously reported values (Yu, W. W. et al. Chem. Mater. 2003, 15 (14), 2854-2860). FIG. 13 shows the data for MNP@QD575 and MNP@QD635. The range of QDs per MNP@QD assembly was estimated from NTA measurements of the PL intensity distribution (vide supra for FIG. 20) for QD635 (1 000±400 QDs per MNP) and QD575 (9 200±3 700 QDs per MNP). A pull-down assay that looked at the absorbance of excess QDs in the supernatant after MNP@QD assembly suggested values of 12 000±200 QD635 per MNP and 30 000±2 700 QD575 per MNP, which may be deemed unrealistically high. In contrast, the values derived from FIG. 13 are consistent with full coverage of the MNP surface area. Assuming the MNPs are spheres with a diameter equal to their hydrodynamic diameter from NTA measurements, the maximum loading of QDs is ~7 100 for QD575 and ~2 500 for QD635. However, the real MNPs are not ideal spheres and QDs may embed within the dextran layer (not just on its surface), increasing the overall loading capacity.

NMR Characterization of API-Dex

Figure 14:
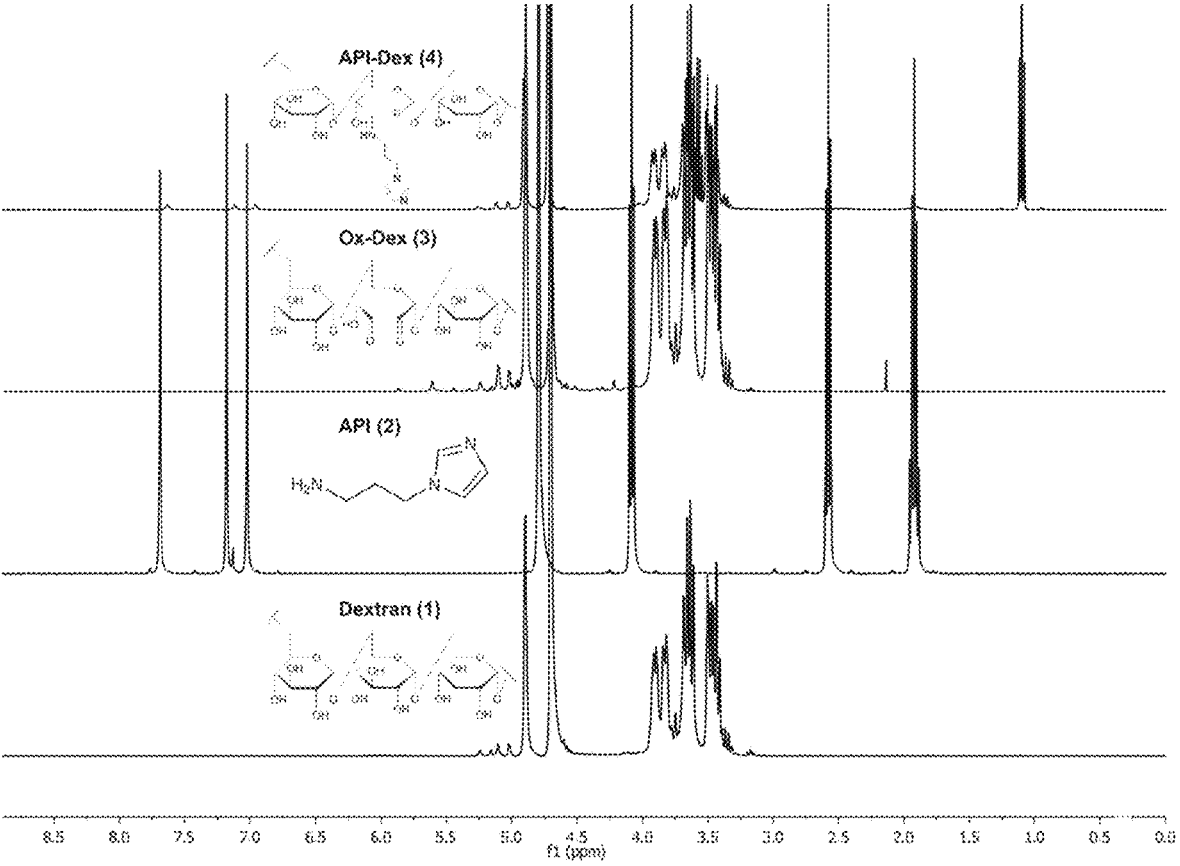
FIG. 14 shows $^1H$ NMR spectra (400 MHz, $D_2O$) for exemplary API-modified dextran and the starting and intermediate materials.

Proton NMR data for API-Dex and the starting materials are summarized below and in FIG. 14. The spectrum for the API-Dex shows the expected aromatic-ring proton resonances from imidazole. The resonances are also broadened, consistent with a polymer. The integration suggests ~4 API groups per dextran chain (calculated assuming the anomeric proton ($\delta$ 4.91) is normalized to 61 protons for a 10 000 MW dextran), although there is batch-to-batch variation.

Dextran (1): $^1$H NMR (400 MHz, $D_2O$) $\delta$ 4.90 (d, J=3.7 Hz, 2H), 3.95-3.89 (m, 1H), 3.86-3.78 (m, 1H), 3.72-3.57 (m, 5H), 3.53-3.38 (m, 4H).

API (2): $^1$H NMR (400 MHz, $D_2O$) $\delta$ 7.69 (t, J=1.3 Hz, 1H), 7.18 (t, J=1.4 Hz, 1H), 7.05-6.99 (m, 1H), 4.08 (t, J=7.0 Hz, 2H), 2.63-2.53 (m, 2H), 1.92 (tt, J=9.0, 6.1 Hz, 2H). It is noted that amine protons were not observed as they exchanged with the $D_2O$.

Oxidized dextran (3): $^1$H NMR (400 MHz, $D_2O$) $\delta$ 9.64 (s, OH), 9.16 (s, OH), 8.36 (s, OH), 5.86 (s, OH), 5.59 (d, J=10.5 Hz, 1H), 5.44 (s, OH), 5.33 (d, J=8.5 Hz, OH), 5.24 (d, J=4.1 Hz, 1H), 5.16 (d, J=3.9 Hz, OH), 5.14-5.06 (m, 4H), 5.02 (d, J=3.9 Hz, 3H), 4.89 (d, J=3.7 Hz, 62H), 3.97-3.86 (m, 47H), 3.82 (ddd, J=10.0, 4.5, 1.8 Hz, 41H), 3.73-3.56 (m, 101H), 3.54-3.36 (m, 105H). It is noted that peaks at 9.64, 9.16, and 8.36 ppm had integrations of 0.03, 0.02, and 0.03 ppm, respectively.

API-modified dextran (4): $^1$H NMR (400 MHz, $D_2O$) $\delta$ 7.63 (s, 1H), 7.12 (s, 1H), 6.96 (s, 1H), 4.91 (d, J=3.7 Hz, 16H), 3.97-3.87 (m, 9H), 3.87-3.80 (m, 7H), 3.74-3.61 (m, 25H), 3.54-3.39 (m, 27H), 2.92-2.22 (m, 2H), 1.91 (s, 3H).

Overcoating with API-Dex

Figures 15A, 15B, 15C, 15D, 15E, 15F:
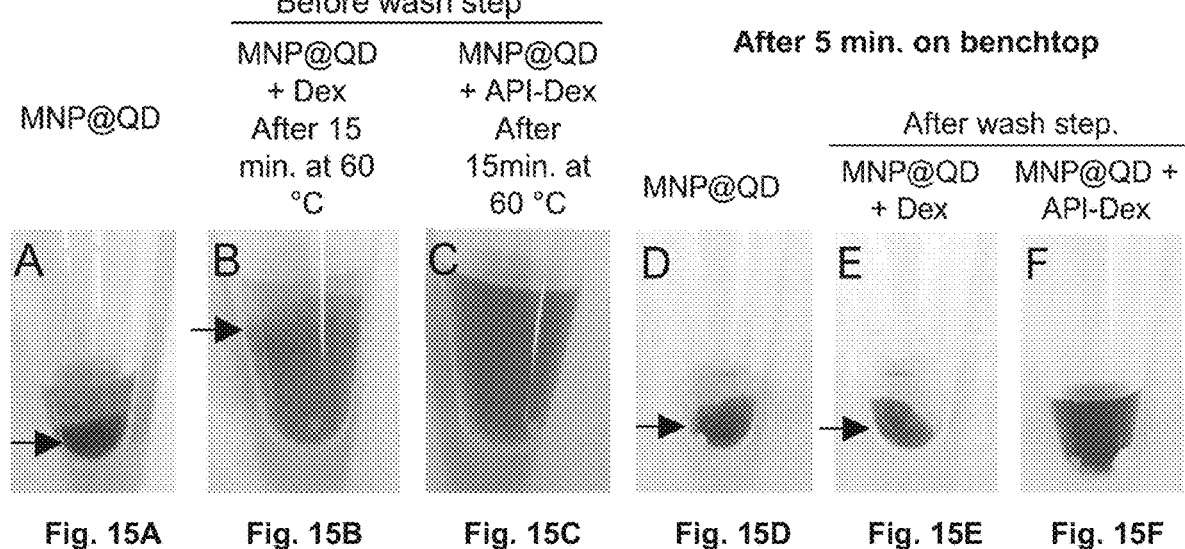
FIGS. 15A-F show colloidal stability of exemplary MNP@QD over-coated with API-modified dextran (API-Dex).

FIG. 15 shows photographs that reflect the colloidal stability of MNP@QDs without and with overcoating with API-Dex. The API-Dex imparts improved colloidal stability compared with MNP@QDs or with the addition of unmodified dextran.

Additional Characterization of MNP@QDs

Figure 16:
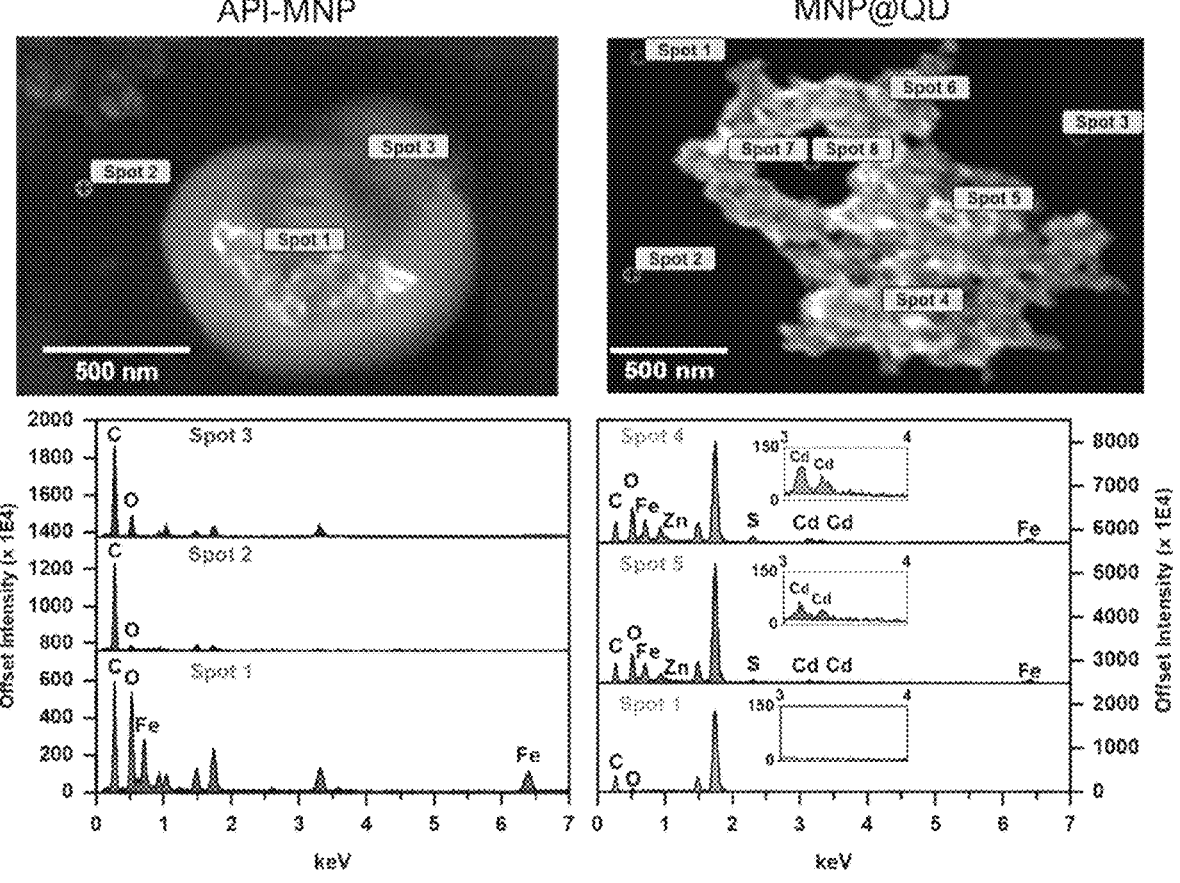
FIG. 16 shows SEM-EDX point analysis of exemplary API-MNP and MNP@QD. Spots represent different regions of the SEM images that were analyzed by EDX. In the exemplary MNP@QD EDX figure, Spot 4 and 5 were chosen to represent the MNP@QD, and Spots 6 and 7 provided analogous spectra. Inset graphs represent the 3-4 keV range. Likewise, Spot 1 was chosen to represent the background and substrate, and Spots 2, 3, and 8 provided analogous spectra.

FIG. 16 shows scanning electron microscopy (SEM) images of API-MNP and MNP@QD assemblies. The SEM imaging modality and sample preparation is not well-suited to these samples, so the images do not reliably depict the morphology of the particles (see the TEM images and NTA data in FIG. 3). The MNP@QD sample in FIG. 16 is an aggregate of multiple particles. The SEM imaging experiment was primarily undertaken for the purpose of energy-dispersive x-ray (EDX) analysis. The EDX analysis of the MNP indicated the presence of Fe and O, consistent with the iron oxide composition (Spot 1). Analysis of the MNP@QD indicated the presence of Fe, O, Zn, S, and Cd, consistent with a composite of iron oxide MNP and QDs (Spots 4-7). (Se signals were too weak to observe.) Regions of the images without nanoparticle material (Spots 2 and 3 for API-MNP; Spots 1, 2, 3, and 8 for MNP@QD) did not show these elements.

Figure 17:
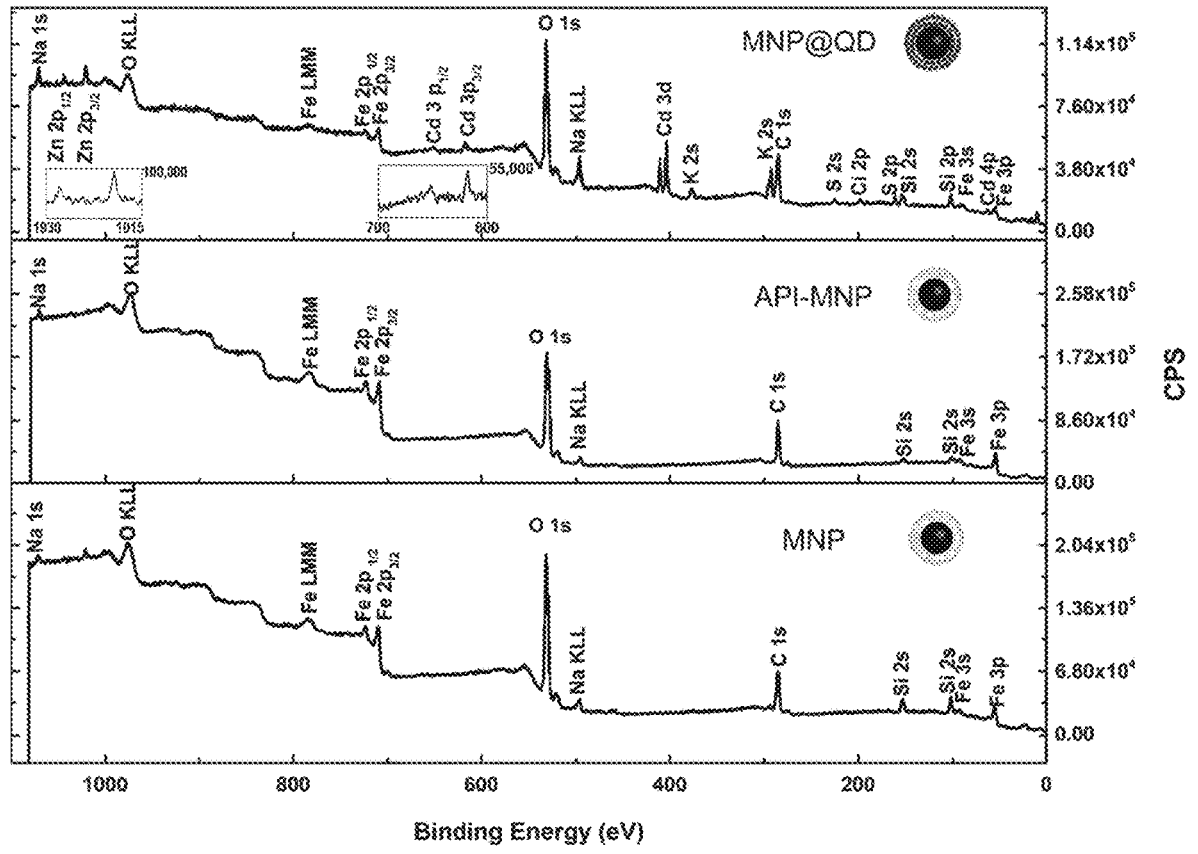
FIG. 17 shows XPS elemental analysis of exemplary MNP, API-MNP, and MNP@QD (No API-Dex over-coating). Peaks are labelled according to the element. Peaks corresponding to QDs (Zn, Cd, S) are labelled as such. Peaks corresponding to MNPs (Fe, O, C) are labelled as such. Peaks corresponding to the glass background (Si) and potassium (K) or sodium (Na) salts are labelled as such.

X-ray photoelectron spectroscopy (XPS) was used to confirm the EDX results and done on samples of unmodified MNP, API-MNP, and MNP@QD. As seen in FIG. 17, all samples showed characteristic peaks (2p, 3s, 3p) for Fe. Only the MNP@QD sample showed peaks characteristic of the QDs: Cd (3p, 3d, 4p), S (2s, 2p), and Zn (2p). Again, Se signals were too weak to observe.)

Figure 18:
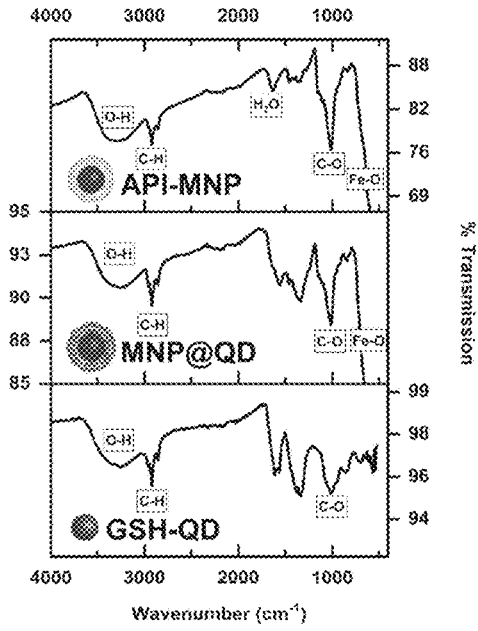
FIG. 18 shows stacked ATR-IR spectra for exemplary API-MNP, MNP@QD, and GSH-QD. Fe—O, C—O, C—H, and O—H bond stretching vibrations are labelled where applicable.

The MNP@QD (where the QDs were GSH-QD605) were also characterized by infrared absorption spectroscopy (ATR-IR) and compared to GSH-QDs and API-MNP, as shown in FIG. 18. The MNP@QD sample showed peaks characteristic of both the GSH-QDs and the API-MNP. These peaks included resonances at 1560 cm$^{-1}$ and 1345 cm$^{-1}$ (GSH-QDs and MNP@QD), a strong and broad peak at 550 cm$^{-1}$ (API-MNP and MNP@QD; indicative of Fe—O vibration modes in the iron oxide), and a strong and sharp resonance at 1010 cm$^{-1}$ (API-MNP and MNP@QD; a C—O stretching vibration of dextran). As expected, all samples had resonances at ~3300 cm$^{-1}$ and ~2900 cm$^{-1}$, corresponding to O—H and C—H stretching vibrations. A water bending peak at 1650 cm$^{-1}$ was prevalent for the API-MNPs but less so for the MNP@QDs and GSH-QDs. Overall, the data showed that the QDs in the MNP@QD assemblies retained many of their GSH ligands upon assembly with the API-modified MNPs.

Nanoparticle Tracking Analysis (NTA)

NTA sizing data for MNP@QD605 and MNP@QD635 assemblies (complementing the data for MNP@QD575 in FIG. 3) are shown in FIG. 19.

Immunomagnetic Cell Isolation and Imaging

Figure 1C:
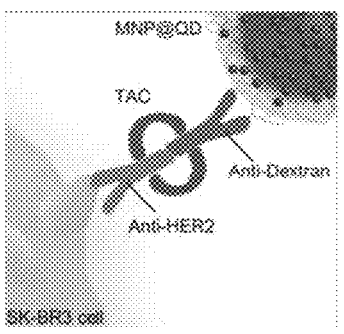
FIG. 1C is a zoomed view of the TAC-mediated binding.
Figure 1D:
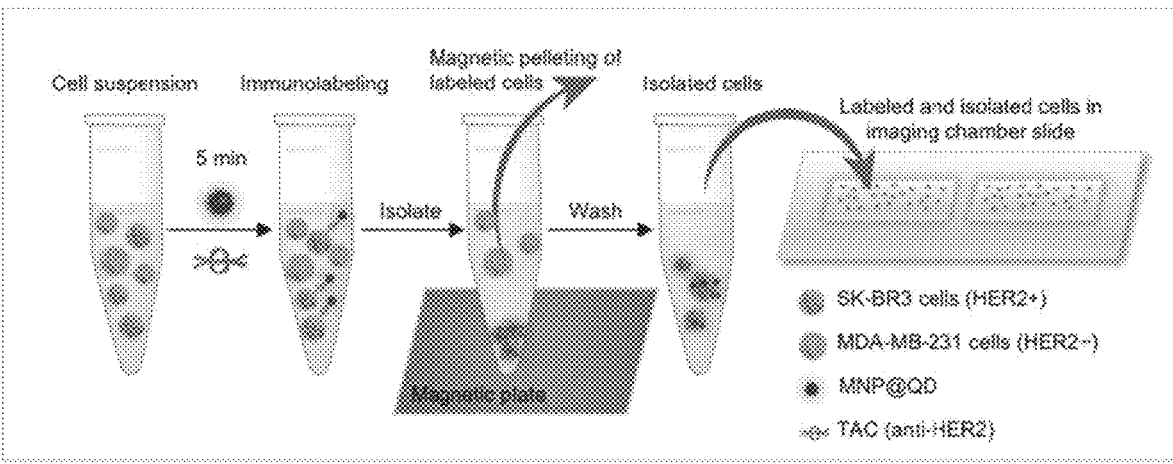
FIG. 1D is a diagram illustrating the steps in the cell counting assay. TAC and MNP@QD are added to a sample cell suspension and the target cells are pelleted magnetically, washed, resuspended, and transferred to a chamber slide for enumeration on the SIP. The assay is demonstrated with a mixture of HER2-positive and HER2-negative breast cancer cells.
Figure 4:
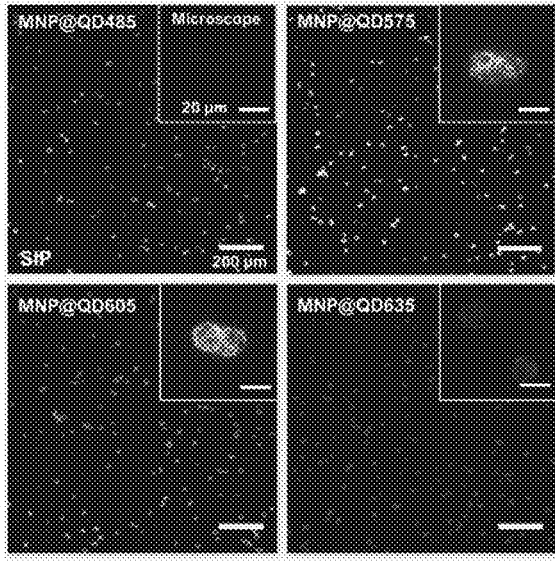
FIG. 4 shows smartphone (main images, scale bar=200 μm) and microscope images (insets, scale bar=20 μm) of fixed SK-BR3 cells isolated with exemplary MNP@QDs of various colors: QD485 (top left), QD575 (top right), QD605 (bottom left), and QD635 (bottom right) shows up as blue, yellow, orange, and red, respectively, where the notation QDA refers to the wavelength of peak PL emission for the QD. The smartphone images were acquired in RGB color format. Microscope images can be pseudo-colored from the measured monochrome intensity values.

Fixed SK-BR3 breast cancer cells were chosen as a model cell line to demonstrate immunomagnetic cell isolation and imaging on the SIP. This cell line overexpresses the HER2 antigen and was therefore targeted with an anti-HER2 antibody. The anti-HER2 was conjugated to the MNP@QD as part of a bifunctional TAC with an anti-dextran antibody (see FIG. 1C). MNP@QDs were prepared in four different PL emission colors (blue, QD485; yellow, QD575; orange, QD605; red, QD635). Fixed SK-BR3 cells were incubated with TAC conjugates of one of the colors of MNP@QD for 5 min, magnetically pelleted, washed, resuspended in PBS buffer, and an aliquot (10 µL) pipetted into a chamber slide. FIG. 4 shows representative images of the isolated cells acquired with the SIP, and the insets show examples of high-magnification images of the isolated cells acquired from a research-grade microscope. The signal-to-noise ratios (SNRs) on the SIP for the four colors of MNP@QDs were 7±3 (±SD), 8±3, 14±5, 9±3 for cells labeled with MNP@QD485, MNP@QD575, MNP@QD605, and MNP@QD635, respectively.

Figure 23A:
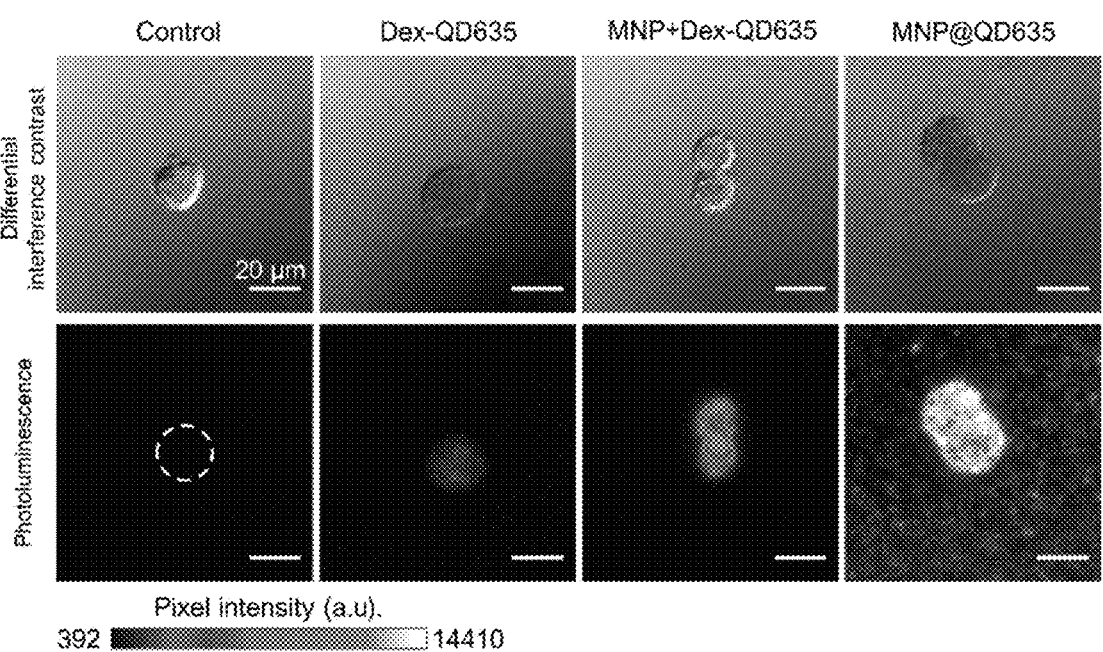
FIG. 23A shows optical microscopy imaging (differential interference contrast, photoluminescence) of labeled SK-BR3 cells. Controls are unlabelled SK-BR3 cells; the cell is outlined with a dashed circle. A pixel-calibration bar is included for comparison purposes. Scale bar=20 μm. All images were acquired under the same microscope and camera settings. Microscope images are false-colored from the measured monochrome intensity values.
Figure 23B:
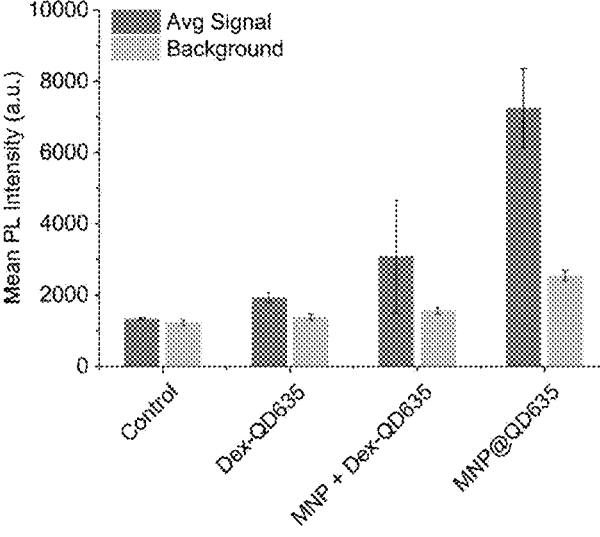
FIG. 23B shows bar graph representation of average PL signal and background for each SK-BR3 labeling condition. A minimum of 20 cells were analyzed from images acquired at a lower magnification (10×).

MNP@QD635 composites were compared to other formats for cell isolation and imaging using a research-grade fluorescence microscope (FIG. 23). Unlabeled cells (i.e. imaged via autofluorescence) had a SNR of 3.5±0.2 (±1 standard deviation). Cells immunolabeled with individual QD-TAC conjugates had a SNR of 9±1, and cells isolated and labeled with a mixture (not composite) of MNP-TAC conjugates and QD-TAC conjugates had a SNR of 16±7. In contrast, the MNP@QD composites provided a vastly superior SNR of 40±17. All imaging was done with the same microscope settings and under the same conditions.

PL Excitation and Emission Spectra

Figures 21A, 21B:
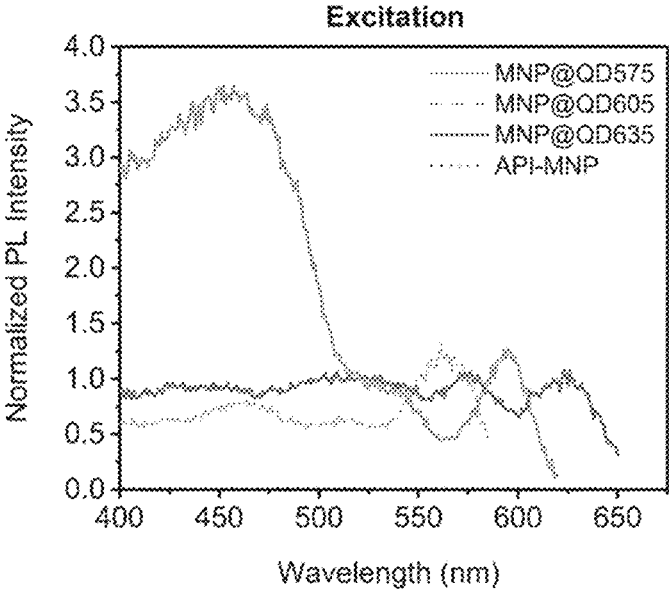
FIG. 21A shows PL excitation spectra for various colors of exemplary MNP@QD.
FIG. 21B shows PL excitation spectra for the corresponding His-QDλ. The QD colors measured were λ=575 nm, 605 nm, and 635 nm.

FIG. 21 compares the excitation spectra of MNP@QD assemblies (for QD575, QD605, QD635) and the corresponding His-coated QDs. The first and second exciton peaks appear at the same spectral positions. The largest difference between the two sets of spectra is the apparent attenuation of the excitation spectrum intensity in the blue-green region of the spectrum (relative to the first exciton peak). This difference is a result of an inner filter effect from scattering of the excitation light by the MNP@QDs (primarily the MNP component).

Figure 22:
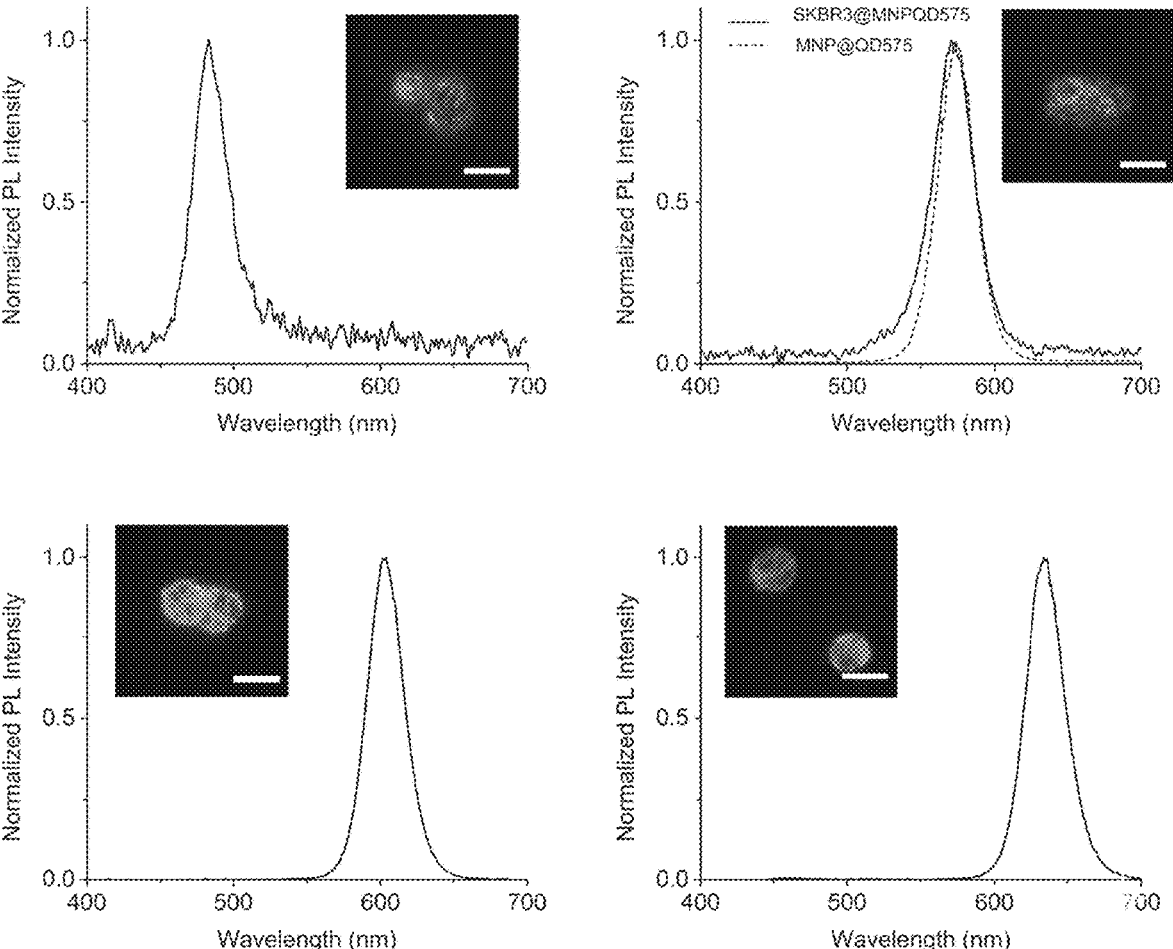
FIG. 22 shows PL emission spectra for fixed SK-BR3 cells labeled with exemplary MNP@QDλ (λ=485 nm, 575 nm, 605 nm, and 635 nm). The spectrum for MNP@QD485 was measured directly from labeled cells. The spectrum for MNP@QD575 was measured from both the assemblies in bulk solution and from labeled cells. The spectra for MNP@QD605 and MNP@QD635 were measured from assemblies in bulk solution.

FIG. 22 shows PL emission spectra for the MNP@QDs (for QD485, QD575, QD605, QD635), measured post-immunolabeling of SK-BR3 cells. As shown for MNP@QD575, the PL emission spectrum measured from a cell does not differ from that measured for the MNP@QD in bulk solution (no cells).

MNP@QD Versus QD and MNP+QD

FIG. 23 compares the signal and background levels for TAC-HER2-mediated SK-BR3 labeling with QDs alone (Dex-QD635), MNP and QDs together (not composite), and composite MNP@QD, with imaging performed on a research grade microscope.

Live Cell Counting

Figure 5A:
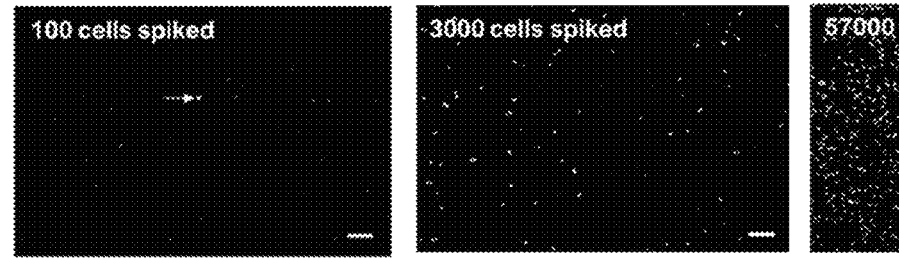
FIG. 5A shows SIP images of increasing numbers of SK-BR3 cells isolated with exemplary MNP@QDs. A single cell is indicated with the arrow for the 100-cell sample. Scale bar=200 μm. Each image represents an area of 2×3 mm².
Figure 5B:
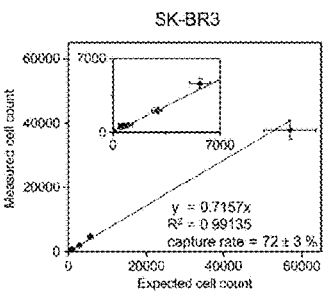
FIG. 5B shows quantification of an increasing number of live SK-BR3 cells (HER2+).
Figure 5C:
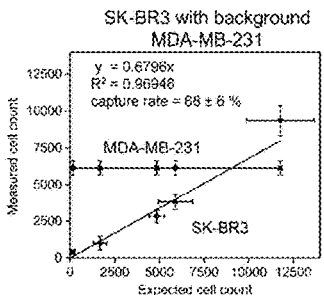
FIG. 5C shows quantification of an increasing number of live SK-BR3 cells in samples spiked with a background of 6140±470 live MDA-MB-231 cells (HER2-).
Figure 5D:
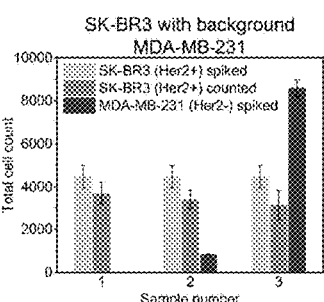
FIG. 5D shows quantification of a constant level of live SK-BR3 cells with increasing background of live MDA-MB-231 (HER2-) cells. All samples were in separation buffer. Additional smartphone images for the assays in panels B-D are shown in FIGS. 24-26.
Figure 10:
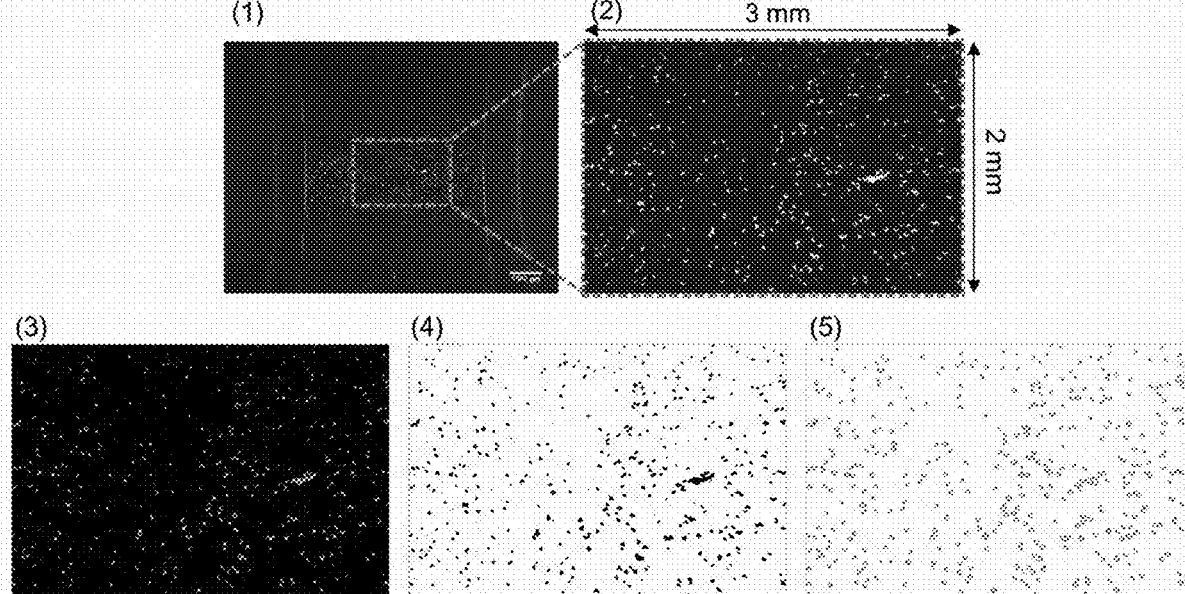
FIG. 10 shows cell counting steps in ImageJ. Step (1): image of exemplary MNP@QD-labeled cells acquired with the SIP (background subtracted). The image scale was set to 0.392 pixel/μm², as determined using the known size of DAPI stained cells that were first imaged on a calibrated microscope and subsequently on the SIP. Step (2): A 2×3 mm² region of interest was defined. The internal height of the chamber is 0.1 mm, so the total volume analyzed was 0.6 μL. Step (3): the color image was converted to an 8-bit image and a threshold value set for pixel intensity, followed by masking the objects. The threshold value is set such that the background fluorescence is set to zero. Step (4): the threshold was applied followed by the watershed function. Step (5): the particles were analyzed, stipulating a minimum size of 125 μm² and a circularity in the range 0.50-1.00 (a perfect circle has a value of unity).

The MNP@QD composites and SIP were tested for live cell isolation and counting. The same procedure used for fixed cells was repeated with live SK-BR3 cells. FIGS. 5A-B show representative SIP images of an increasing number of isolated live SK-BR3 cells and a plot of the number of cells counted versus the number of cells spiked. The data was linear (correlation coefficient of $R^2=0.99$) with a slope that corresponded to a live-cell capture efficiency of 72±3%. Isolation and counting of live SK-BR3 cells was also assessed in the presence of a constant number (~6100) of background MDA-MB-231 breast cancer cells. MDA-MB-231 cells do not express HER2 and therefore should not have been immunomagnetically isolated. As shown in FIG. 5C, the linear trend ($R^2=0.97$) and the SK-BR3 capture efficiency (68±6%) were maintained with the high number of background MDA-MB-231 cells. As another test of the specificity of SK-BR3 isolation, counting assays were done with a constant number of spiked SK-BR3 cells and an increasing background of MDA-MB-231 cells. FIG. 5D shows that spikes of ~4500 (±500) SK-BR3 cells were successfully counted with recovery between 70-83% against backgrounds of ~800 and ~8600 MDA-MB-231 cells, consistent with the data in FIGS. 5B-C. In a one-tailed t-test, there was no statistically significant difference in the mean number of cells enumerated between each of the samples (determined by a one-way analysis of variance for a significance level of a 0.10).

SIP Images from Cell-Counting Assays

Figure 24:
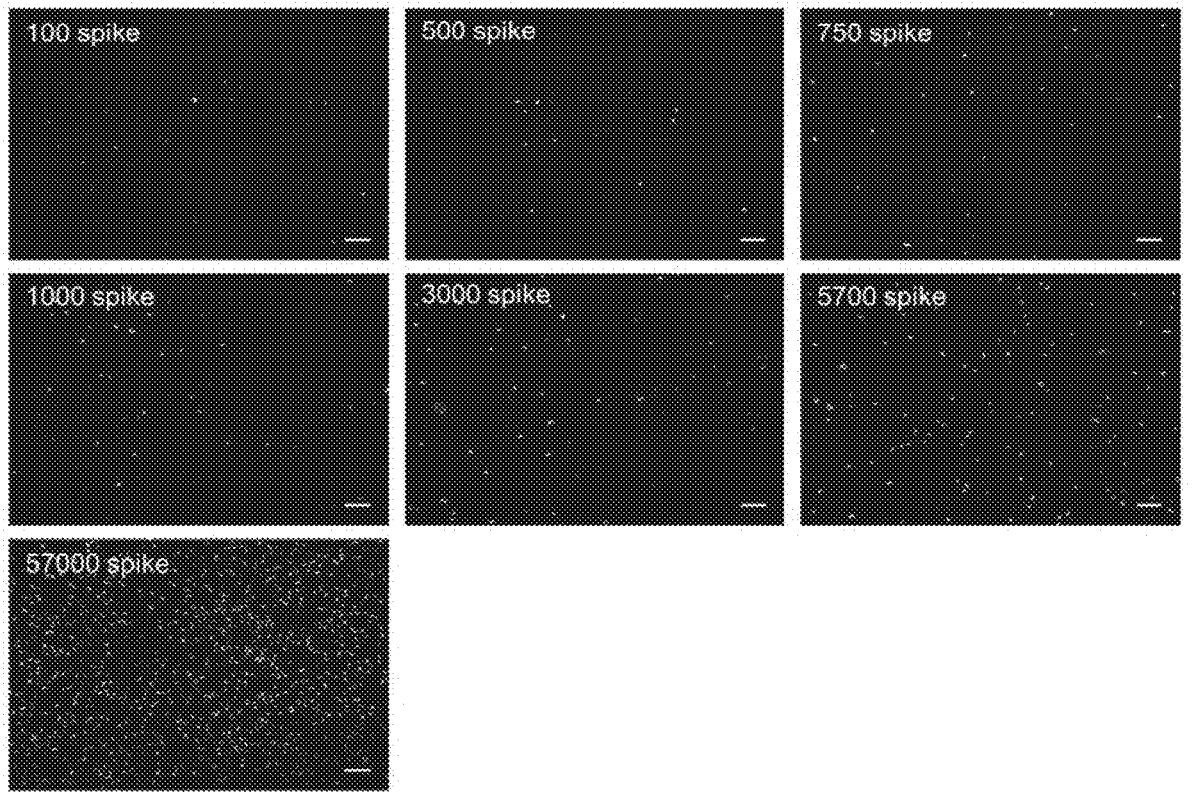
FIG. 24 shows representative SIP images of exemplary MNP@QD605 isolated cells from FIG. 5B. Scale bars=200 μm.
Figure 25:
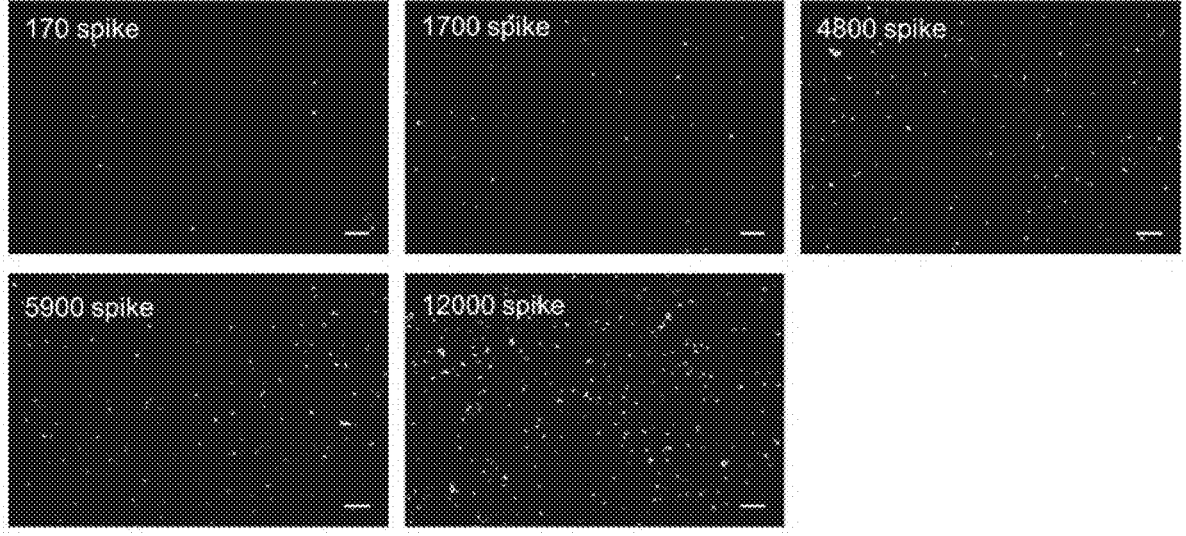
FIG. 25 shows representative SIP images of exemplary MNP@QD635 isolated cells from FIG. 5C. Scale bars=200 μm.
Figure 26:
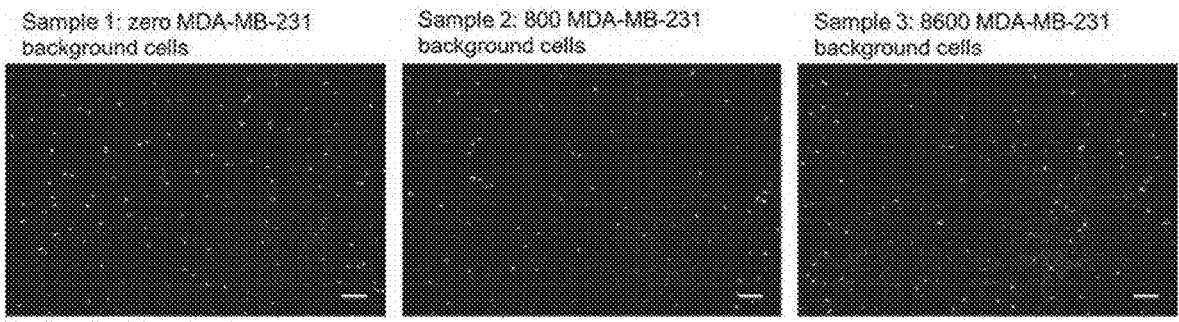
FIG. 26 shows representative SIP images of exemplary MNP@QD575 isolated cells from FIG. 5D. Scale bars=200 μm.

FIGS. 24-26 show representative PL images from the SIP for the experiments in FIG. 5.

Discussion

The present assay of the application can quantify cells between a lower limit of $\sim 10^2$-$10^3$ cells/mL and an upper limit of $\sim 10^7$ cells/mL. The upper limit of this range is set by the requirement (for the counting algorithm) for dark space between individual cells in SIP PL images. The lower limit is set by the stochastic probability of finding an individual cell within the 0.6 µL volume of the counting field of view (~1700 cells/mL) or within the 10 µL volume of the chamber slide that can be searched for an individual cell (~100 cells/mL). These limits are the cell concentrations after magnetic isolation. The cell concentrations in the original sample can be much lower, provided that the magnetic isolation is efficient and the magnetic isolate is resuspended in a much smaller volume than the original sample. For this study, the volume ratio between samples and resuspended magnet isolates was 1:2, showing that there is significant room for magnetic pre-concentration with larger sample volumes (e.g. a 2 mL-sample could be magnetically concentrated 100-fold by resuspension in 20 µL). This assay was also simple, consisting of only four steps (incubation, magnetic pelleting, single wash, and imaging) with a total assay time under 15 min.

The SIP disclosed herein was simple in design, amenable to manufacturing, and adaptable to many models of smartphone (by varying the precise dimensions of the top-stage). It also had a small footprint ($20 \times 10$ cm$^2$) and was approximately one third of the cost of the smartphone. In principle, the smartphone could be replaced with a simple CMOS imaging sensor, but this approach would lack the processing, memory, connectivity, and other versatility advantages of a smartphone. The chamber slide sample holder was the same dimensions as a standard microscope slide ($25 \times 75$ mm$^2$), such that many other sample methods and devices (e.g. microfluidic chips) are compatible with the SIP or straightforward modifications thereof.

Although several forms of imaging and bioanalysis are possible with smartphones (see Petryayeva, E.; Algar, W. R. RSC Adv. 2015, 5 (28), 22256-22282; Vashist, S. K. et al.

Anal. Bioanal. Chem. 2014, 406 (14), 3263-3277; Erickson, D. et al. Lab Chip 2014, 14 (17), 3159-3164), smartphone cameras are neither designed nor optimized for PL imaging. This fact motivated the use of an app (Camera FV-5) that enabled control over ISO and shutter speed (i.e. exposure time) settings, and supported imaging in RAW format to avoid challenges from auto-correction of images. The non-optimal PL imaging with a smartphone motivated the design of the MNP@QD assemblies. The assembly of hundreds to thousands of QDs per MNP resulted in ultra-bright nanoparticles that compensated for any sensitivity deficiency of the smartphone camera and the simple optics in the SIP. The combined magnetic and bright PL properties within a single vector represented another simplifying aspect of the supraparticle assembly. Separate magnetic and luminescent materials were not required and, even though unbound MNP@QDs were magnetically isolated in parallel with cell-bound MNP@QDs, isolated cells were visible above background PL with high SNR. This result is attributed to the cell concentrating many MNP@QD assemblies, and thus a very large number of QDs, into a relatively small number of image pixels.

Another advantage of the present MNP@QD materials is that they were largely self-assembled. The stock materials are ligand-coated QDs, API-modified MNPs, API-modified dextran, and TAC reagents. Once these materials are on hand, immunoconjugates of MNP@QD can be prepared without covalent chemistry, with assembly driven instead by affinity interactions. The exclusion of covalent chemistry necessitates fewer steps in the process, simpler purification, and makes it more reproducible and amenable to scale-up. It also potentiates on-demand preparation of MNP@QD immunoconjugates using whatever combination of cell-targeting antibody and QD color is desired. Use of the TAC is also advantageous because it puts MNP@QD-conjugated antibodies in a productive orientation for binding to their antigen targets, which is a frequent and significant challenge with covalent conjugation of antibodies to nanoparticles (Algar, W. R. et al. Bioconjug. Chem. 2011, 22 (5), 825-858).

In addition to their self-assembled preparation, the present MNP@QD materials are advantageous in their size and in the intrinsic optical properties of the QDs. Compared to larger magnetic-fluorescent particles (e.g. Song, E. Q. et al. ACS Nano 2011, 5 (2), 761-770; Dong, X.; Zheng, Y.; Huang, Y.; Chen, X.; Jing, X. Anal. Biochem. 2010, 405 (2), 207-212; Chung, T. H.; Chang, J. Y.; Lee, W. C. J. Magn. Magn. Mater. 2009, 321 (10), 1635-1638), smaller particles are less prone to aggregating and clumping isolated cells, which would hinder counting, and also block less of the cell surface, which is a benefit to applications in which multiple antigens are to be measured. Compared to magnetic-fluorescent materials based on organic dyes (e.g. Di Corato, R. et al. Macromol. Biosci. 2009, 9 (10), 952-958; Bertorelle, F. et al. Langmuir 2006, 22 (12), 5385-5391), the QDs are expected to be brighter, more resistant to photobleaching, and better suited to multicolor analyses. The brightness of the MNP@QD materials also enabled this first example of a magneto-immunofluorescent cell counting assay on a smartphone. Previous reports of smartphone-based cell counting have used magnetophoresis with non-specific fluorescent staining (Knowlton, S. et al. Lab Chip 2017, 17 (16), 2839-2851), immunofluorescent labeling with surface-immobilized capture antibodies rather than magnetic isolation (Zhu, H.; Sikora, U.; Ozcan, A. Analyst 2012, 137 (11), 2541-2544), or non-specific staining without magnetism or immunocapture (Zhu, H. et al. Anal. Chem. 2011, 83 (17), 6641-6647). Although each approach has its use, the present all-in-one magnetic isolation and immunofluorescent staining requires only one antibody against the target cell and does not require a fluidic system.

The MNP@QD materials and SIP are useful for a simple and effective method for multiplexed isolation, counting, and immunoprofiling of cells. For example, the preparation of MNP@QD with different colors of QDs (e.g. blue, green, yellow, orange, or red emitters) paired with different target-ing antibodies is useful for encoding the phenotypes of isolated cells based on their expression of cancer-relevant antigens such as Mucin 1 (MUC1), epithelial cell adhesion molecule (EpCAM), epidermal growth factor receptor (EGFR), estrogen receptor (ER), and progesterone receptor (PR). The same concept can also be applied beyond cancer; for example, assays of hematopoietic progenitor cells or immune cells (e.g. HIV/AIDS), and multiplexed screening assays for pathogenic microorganisms. The spectrally narrow PL emission of QDs and the efficient parallel excitation of multiple colors of QDs at a single wavelength make QDs particularly well-suited to these types of applications.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A particle assembly comprising:
   a. a nanoparticle core that is responsive to a magnetic field;
   b. a first polymer coating surrounding the core, the first polymer coating comprising a first polymer, wherein the first polymer comprises imidazole functional groups to bind quantum dots;
   c. a second polymer over-coating external to the first polymer coating, the second polymer over-coating comprising a second polymer wherein the second polymer comprises imidazole functional groups to bind the quantum dots; and
   d. a corona of quantum dots surrounding the core wherein the quantum dots are bound to and between the first polymer coating and the second polymer over-coating,
   wherein the particle assembly is cell-compatible,
   wherein the particle assembly has diameter greater than 100 nm, and
   wherein the imidazole groups are covalently bound to the first and second polymers.

2. The particle assembly of claim 1, wherein the core comprises metal elements and the metal elements are present as ferrofluids, colloids or particles in suspension.

3. The particle assembly of claim 1, wherein the core comprises iron oxide nanoparticles.

4. The particle assembly of claim 1, wherein the core is paramagnetic or superparamagnetic.

5. The particle assembly of claim 1, wherein the first and second polymers non-covalently bind the quantum dots.

6. The particle assembly of claim 1, wherein the first and second polymers are independently, poly(ethylene glycol) (PEG), PEG derivatives, poly(carboxybetaine), dextran, starch, heparin, chitin, cellulose, other polymers of cyclic sugars, synthetic polymers with high anti-fouling properties, peptides or nucleic acids.

7. The particle assembly of claim 6, wherein the first and second polymers are the same and/or are dextran.

8. The particle assembly of claim 1, wherein the first polymer is cross-linked.

9. The particle assembly of claim 1, wherein the quantum dots comprise Cd, Se, Zn and/or S.

10. The particle assembly of claim 1, wherein the quantum dots are ligand stabilized.

11. The particle assembly of claim 1, further comprising a bispecific antibody complex comprising an antibody that binds to the second polymer over-coating, and optionally the first polymer coating, and an antibody that binds to a target antigen.

12. A method of preparing the particle assembly of claim 1 comprising:
a. combining the core coated with the first polymer coating and the quantum dots under conditions for the self-assembly of the quantum dots in a corona surrounding the core coated with the first polymer coating to provide a particle-quantum dot assembly; and
b. separating unbound quantum dots from the particle-quantum dot assembly; and
c. coating the separated particle-quantum dot assembly from b. with the second polymer over-coating.

13. The method of claim 12, wherein the first polymer is dextran.

14. A method for detecting and, optionally quantifying, a target antigen in a mixture comprising:
a. combining the mixture with the particle assembly of claim 1 and a bispecific antibody complex (BAC) comprising an antibody that binds to the second polymer over-coating, and optionally the first polymer coating, and an antibody that binds to the target antigen to form a particle assembly-BAC-target antigen conjugate;
b. applying a magnet or a magnetic field to the mixture to separate the particle assembly-BAC-target antigen conjugate from the mixture;
c. isolating the particle assembly-BAC-target antigen conjugate; and
d. imaging the particle assembly-BAC-target antigen conjugate,
wherein a positive image indicates a presence of the target antigen in the mixture, and optionally, the intensity of the positive image is used to quantify the target antigen in the mixture.

15. The method of claim 14, wherein the imaging is performed using an imaging platform, the imaging platform including:

an imaging device having a camera;
an imaging housing having:
a sample mount shaped to hold a sample of the particle assembly-BAC-target antigen conjugate in a sample position, and
an imaging platform mount shaped to hold the imaging device in an imaging device position, the imaging device position directing the camera towards the sample position;
a laser source positioned to illuminate the sample position; and
a power source coupled to the laser source to provide a power supply to the laser source.

16. The method of claim 15, wherein the imaging platform further includes at least one beam-shaping lens between the laser source and the sample position, at least one magnifying lens between the sample position and the imaging device position, and an emission filter between the at least one magnifying lens and the imaging device position.

17. The method of claim 15, wherein the imaging platform mount further includes a stage shaped to support a body of the imaging device, the stage positioned above the sample mount and selectively vertically translatable relative the sample mount.

18. The method of claim 15, wherein the imaging housing encloses the sample position and the laser source within a housing interior formed by a set of sidewalls overlaid by the stage, the stage including an imaging aperture through which the imaging device position directs the camera.

19. The method of claim 16, wherein the emission filter is removably received in the imaging aperture and selectively vertically translatable along with the stage, the emission filter slidably removable from the imaging aperture along a filter removal path which does not pass through the imaging device position.

20. The method of claim 15, wherein the imaging device is a smartphone.

21. The method of claim 15, wherein an intensity of the laser source is adjustable by modifying the power supply.

22. The method of claim 21, wherein the imaging platform further includes a rheostat coupled between the laser source and the power source, and the power supply may be modified using the rheostat.

23. The method of claim 15, wherein the imaging platform further includes at least one laser dial coupled to the laser source to adjust an angle of the laser and a distance between the laser source and the sample position.

24. The method of claim 15, wherein the sample mount is shaped to removably receive a chamber slide in which the sample is contained, the chamber slide slidably removable from the housing along a chamber removal path which does not pass through the imaging device position.

25. A composition comprising a plurality of particle assemblies, wherein the particle assemblies are as defined in claim 1.

\* \* \* \* \*